United States Patent
Scherer et al.

(10) Patent No.: US 11,254,984 B2
(45) Date of Patent: Feb. 22, 2022

(54) BIOMARKERS FOR AUTISM SPECTRUM DISORDERS

(71) Applicants: The Hospital for Sick Children, Toronto (CA); Centre for Addiction and Mental Health, Toronto (CA)

(72) Inventors: Stephen W Scherer, Toronto (CA); John B Vincent, Toronto (CA)

(73) Assignee: The Hospital for Sick Children, Toronto (CA)

(*) Notice: Subject to any disclaimer, the term of this patent is extended or adjusted under 35 U.S.C. 154(b) by 1 day.

(21) Appl. No.: 16/694,314

(22) Filed: Nov. 25, 2019

(65) Prior Publication Data

US 2020/0157628 A1 May 21, 2020

Related U.S. Application Data

(60) Division of application No. 14/630,205, filed on Feb. 24, 2015, now Pat. No. 10,526,653, which is a continuation of application No. 12/681,229, filed as application No. PCT/CA2008/001767 on Oct. 3, 2008, now abandoned.

(60) Provisional application No. 60/960,572, filed on Oct. 4, 2007, provisional application No. 61/008,294, filed on Dec. 20, 2007.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/112* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

PUBLICATIONS

GenBank Record NM_173495, Homo sapiens patched domain containing 1 (PTCHD1, mRNA) Sep. 6, 2006, 2 pages. (Year: 2006).*

* cited by examiner

*Primary Examiner* — Juliet C Switzer
(74) *Attorney, Agent, or Firm* — Gowling WLG (Canada) LLP; Susan Tandan

(57) ABSTRACT

Methods of determining the risk of ASD in an individual are provided which comprise identifying the presence of one or more genomic mutations in one or more of the genes, PTCHD1, SHANK3, NFIA, DPP6, DPP10, DYPD, GPR98, PQBP1, ZNF41 and FTSJ1.

8 Claims, 10 Drawing Sheets
Specification includes a Sequence Listing.

```
GCTCTAGGAT GCTGCGGCAG GTTCTGCACA GGGGCTTGAG GACGTGTTTC  50
TCCCGGCTCG GCCACTTCAT TGCCAGTCAC CCTGTCTTCT TCGCCTCGGC  100
GCCGGTGCTC ATCTCCATCC TGCTCGGCGC CAGCTTCAGC CGCTACCAGG  150
TCGAGGAGAG CGTGGAGCAC CTGCTGGCGC CCCAGCACAG CCTGGCCAAG  200
ATCGAGCGCA ACCTCGTTAA CAGCCTCTTC CCGGTCAACC GCTCCAAGCA  250
CCGTCTCTAC TCGGACCTGC AGACCCCGG GCGCTACGGC CGGGTCATCG   300
TCACCTCCTT CCAGAAAGCC AACATGCTGG ACCAGCATCA CACCGACCTG  350
ATCTTAAAGT TGCATGCTGC TGTCACCAAG ATCCAGGTTC CAAGGCCTGG  400
TTTTAATTAC ACGTTTGCCC ATATATGTAT CCTGAATAAT GATAAGACTT  450
GCATCGTGGA TGACATAGTG CACGTCCTGG AAGAGCTAAA GAATGCTCGG  500
GCCACCAATC GGACCAATTT TGCTATCACA TACCCAATCA CTCACTTAAA  550
GGACGGGAGG GCTGTGTACA ATGGGCACCA GCTTGGGGGC GTCACTGTGC  600
ACAGCAAAGA CCGGGTGAAA TCTGCAGAGG CCATCCAGCT CACCTACTAC  650
CTGCAGTCAA TCAACAGTCT CAATGACATG GTGGCTGAGA GGTGGGAGTC  700
CAGCTTCTGC GACACTGTCA GACTGTTTCA GAAATCCAAC AGCAAAGTCA  750
AAATGTACCC TTACACGTCC TCCTCACTGA GGGAAGATTT CCAGAAGACC  800
AGCCGCGTAT CAGAACGTTA CCTGGTCACC AGCCTGATTC TGGTGGTTAC  850
CATGGCCATC CTGTGTTGCT CTATGCAGGA CTGCGTCCGC AGCAAACCCT  900
GGCTAGGCCT GCTCGGATTG GTGACCATAA GCCTGGCCAC TCTCACTGCA  950
GCCGGGATCA TCAATCTTAC TGGTGGGAAA TATAATTCCA CCTTCCTGGG  1000
AGTCCCTTTC GTCATGCTAG GTCATGGATT ATATGGGACT TTTGAAATGT  1050
TATCCTCCTG GAGGAAAACT AGAGAAGACC AACATGTTAA AGAGAGAACT  1100
GCAGCAGTCT ATGCAGACTC CATGCTCTCC TTTTCTCTCA CCACTGCCAT  1150
GTACCTGGTC ACCTTTGGCA TAGGGGCCAG CCCTTTCACG AACATTGAGG  1200
CAGCCAGGAT TTTCTGCTGC AATTCCTGTA TTGCAATCTT CTTCAACTAC  1250
CTCTATGTAC TCTCGTTTTA TGGTTCCAGC CTAGTGTTCA CTGGCTACAT  1300
AGAAAACAAT TACCAGCATA GTATCTTCTG TAGAAAAGTC CCAAAGCCTG  1350
AGGCATTGCA GGAGAAGCCG GCATGGTACA GGTTTCTCCT GACGGCCAGA  1400
TTCAGTGAGG ACACAGCTGA AGGCGAGGAA GCGAACACTT ACGAGAGTCA  1450
CCTATTGGTA TGTTTCCTCA AACGCTATTA CTGTGACTGG ATAACCAACA  1500
CCTATGTCAA GCCTTTTGTA GTTCTCTTTT ACCTTATTTA TATTTCCTTT  1550
GCCTTAATGG CTATCTGCA GGTCAGTGAA GGGTCAGACC TTAGTAACAT  1600
TGTAGCAACC GCGACACAAA CCATTGAGTA CACTACTGCC CAGCAAAAGT  1650
ACTTCAGCAA CTACAGTCCT GTGATTGGGT TTTACATATA TGAGTCTATA  1700
GAATACTGGA ACACTAGTGT CCAAGAAGAT GTTCTAGAAT ACACCAAGGG  1750
GTTTGTGCGG ATATCCTGGT TTGAGAGCTA TTTAAATTAC CTTCGGAAAC  1800
TCAATGTATC CACTGGCTTG CCTAAGAAAA ATTTCACAGA CATGTTGAGG  1850
AATTCCTTTC TGAAAGCCCC TCAATTTTCA CATTTTCAAG AGGACATCAT  1900
CTTCTCTAAA AAATACAATG ATGAGGTCGA TGTAGTGGCC TCCAGAATGT  1950
TTTTGGTGGC CAAGACCATG GAAACAAACA GAGAAGAACT CTATGATCTC  2000
TTGGAAACCC TGAGGAGACT TTCTGTCACC TCCAAGGTGA AGTTCATCGT  2050
CTTCAATCCG TCCTTTGTAT ACATGGATCG ATATGCCTCC TCTCTGGGAG  2100
CCCCCCTGCA CAACTCCTGC ATCAGTGCTT TGTTCCTGCT CTTCTTCTCG  2150
GCATTCCTGG TGGCAGATTC ACTGATTAAC GTCTGGATCA CTCTCACAGT  2200
TGTGTCCGTG GAGTTTGGAG TGATAGGTTT CATGACATTA TGGAAAGTAG  2250
AACTGGACTG CATTTCTGTG CTATGCTTAA TTTATGGAAT TAATTACACA  2300
ATTGACAATT GTGCTCCAAT GTTATCCACA TTTGTTCTGG CAAGGATTT   2350
CACAAGAACT AAATGGGTAA AAAATGCCCT GGAAGTGCAT GGGGTAGCTA  2400
TTTTACAGAG TTACCTCTGC TATATTGTTG GTCTGATTCC TCTTGCAGCT  2450
GTGCCTTCAA ATCTGACCTG TACACTGTTC AGGTGCTTGT TTTAATAGC   2500
ATTTGTCACC TTCTTTCACT GCTTTGCCAT TTTACCTGTG ATACTGACTT  2550
TCCTGCCACC CTCTAAGAAA AAAGGAAAG AGAAGAAAAA TCCTGAGAAC   2600
CGGGAGGAAA TTGAGTGTGT AGAAATGGTA GATATCGATA GTACCCGTGT  2650
GGTTGACCAA ATTACAACAG TGTGATAATG TCTGCTTGGC ATATTTTCAC  2700
```

Figure 7A

```
CTTAGGTCTT ATCAAGACCA AAGAGATTAT GTTAATGAAA CAATTAAATT 2750
CAAAGTTCTT CCCTTTTTTA AAGATAGGAA ACAGGCATTG CCAAAAAAAA 2800
AAAAAAAAAA AAAAGGAAAG GACAGTGGGG AGAAATGGGC CTGGCATATT 2850
TTCAGTCTTT AAAACAAAGG AGTTGTTATG AGAATTCACA CACACATAGA 2900
CACACACACA CACACACACA CACACACACA CACACACACA CCCTGGGAGA 2950
CCTATAGTCT CTTAAACTAA GATCAAGTAG AAGAAAGCTT ATTAACAAGC 3000
AGGATCCTGC CTTATCCAAA CTGCAGATGT TGCTGGCATT GTGACAAAAC 3050
CCACTGATTG AAAGGTCAAC TGCCAAGGCA GAAACACCTT TAAGCATTGT 3100
TCAAACAATA AGGCTTCCAG AACTTCTGTA GAGCAGTAGC TCCAGTCATG 3150
GTCTGTGGTT TGAGGTTTTA GCTGTCTCAC CTAGCTCCCT AACACTGAAG 3200
GAGATACTTG TGAAAGTTCT GACCAGCAAA AGCAAGCCAG AGCCTTGGAA 3250
ACTGATATGT GGTAGAGTGG CCATCACTCA TGGACTAAAA TTGATTCACC 3300
GCTAAATTTA CCCAGGTGAA GCAGTTTCGT TGTCTAGAAT GAAATTATCA 3350
TATTCCGCCA TTGGTATGCC TTTAACATTT GTATAGTTTG GTTTGCTTAA 3400
AACACCTTAA AACCAATGAC AGCTCCAGCA CTGCAGAATT GGTGTGATTC 3450
TACTTTGGAA TAGCTTGTCA CTTGTCACCA AATGGGTCTG CTTTATTAGT 3500
TACAGCTCTT GGCAGGAGGA TCCAGGGACC CAAACCACA GGGCCAAACC 3550
CAAATACCTG GCATGATGGA GCAAAGCAG GTGTCTACTT GGACCCAGAT 3600
ATAGTGTCTC CATTTTAACA ACAACAACAA AATAGCCAGC TGGTACAGCT 3650
GTTTGCATTG GCCCTACATG CATTTTTTGC ATGGATATCC AGAAACATCT 3700
GCCCACACAA AACTGCGGGG AAAAAAAATG AACACTGAAA TAGTTATTTG 3750
CTGTTGCTTC CAACTTGTAG TGCCAGTCTG CCTTTGCTGT GAAACACACC 3800
TGCTCAGAGA CAGAGAGGGG AAGAAGATCT TTGGTAAGTC TAAGTCCTGA 3850
CGCTGAGAAG CTTTGTAAAA GTGCAGGAG ATAAAGGGCC AAAAGGGAGA 3900
TAGATGGAAA ACACTGGAAA AAGTATTCAC TGATACAAAT CTATCAATGA 3950
TGGCAGTCCA ATTCTCTTGC TAAAGTGGCT GCACCTCACC TTGCTGGTCC 4000
CCCCCACACC TTTTTTGATG TCCTTCTGCG TCATCATAGC AAGGCCCTTC 4050
TGTAAATTAA CAAGCCTAGA TATTTATACT CTTGACTTCC AGTATCTACA 4100
GAAGAATGGT TCATAGATCT AAACAGAAAT GGTTTAGATC TAAAAAGGCT 4150
GTATACGTTG CCCAGGCCCC TGCATTTCTT TAAATTTATA AAAATGAAGC 4200
TAAAACCTGG TTACATTGA AGCAAATATC TACAGTATTT TTCCCTTTTA 4250
GAGATGTAGC TTCCTTAGAC ATCTGTAGTG GTAAGCATTT CCCAAAAGCA 4300
TCTTACCTTT CTGAACCTTA GCAGACATAC TGTGCAGCTT ACCTATCTTC 4350
TGCAGAGGAG GAAACTGAGA CCTAGGAGAA TAAAGTGACT CACTCAGGTC 4400
ACACCACTAA AGGGTTTTCA TCATTTCAGC ATACCTAAGA CAGGGCAGTC 4450
CAATTTTCAG TATTCTCATA AGATGGCTAT TACTCCTCTC AAAATGCATT 4500
TCCAAAGTAG GAACATAGGA CTTCGTTGGC CACAGGGCAG ACATTTTTT 4550
AGTGTCTGGA ATTAAAATGT TTGAGGTTTA GGTTTGCCAT TGTCTTTCCA 4600
AAAGGCCAAA TAATTCAGAT GTAACCACAC CAAGTGCAAA CCTGTGCTTT 4650
CTATTTCACG TACTGTTGTC CATACAGTTC TAAATACATG TGCAGGGGAT 4700
TGTAGCTAAT GCATTACACA GTCGTTCAGT CTTCTCTGCA GACACACTAA 4750
GTGATCATAC CAACGTGTTA TACACTCAAC TAGAAGATAA TAAGCTTTAA 4800
TCTGAGGGCA AGTACAGTCC TGACAAAAGG GCAAGTTTGC ATAATAGATC 4850
TTCGATCAAT TCTCTCTCCA AGGGGCCCGC AACTAGGCTA TTATTCATAA 4900
AACACAACTG AAGAGGGGAT TGGTTTTACT GTTAAATCAT GTGTTGCTAA 4950
ATCATTTTCT GAACAGTGTG TTCTAAATCA GTCATTGATT TAGTGTCAGC 5000
CACGTGGAGC ACCTCGGCTT AAAGCAGCTC CACAAAACCT GACACAACAC 5050
ACACACCAAT TAAATGGATT TTGTTGAGAA TTTAATCATT CAATTTGGTC 5100
AACCAGAATG ACTTCCTGTG GAACTCTGTT TTATGACAGA TAATAGTTTT 5150
CCAACTTGAT TGAGTCTCTG TATACCCTGG GATATTGTAT TTTTTAATGA 5200
AGGGCATTTT CAAACTTGTC AACTTCTCTT TTCAGCACTT GAAATGAAGG 5250
CTTATGGAAT TCTGACTGTG AAATGAATTT TTCTATTGGG AAAAAAAAAA 5300
AAAAA     (SEQ ID NO: 17)
```

Figure 7A cont'd

MLRQVLHRGLRTCFSRLGHFIASHPVFFASAPVLISILLGASFSRYQVEE
SVEHLLAPQHSLAKIERNLVNSLFPVNRSKHRLYSDLQTPGRYGRVIVTS
FQKANMLDQHHTDLILKLHAAVTKIQVPRPGFNYTFAHICILNNDKTCIV
DDIVHVLEELKNARATNRTNFAITYPITHLKDGRAVYNGHQLGGVTVHSK
DRVKSAEAIQLTYYLQSINSLNDMVAERWESSFCDTVRLFQKSNSKVKMY
PYTSSSLREDFQKTSRVSERYLVTSLILVVTMAILCCSMQDCVRSKPWLG
LLGLVTISLATLTAAGIINLTGGKYNSTFLGVPFVMLGHGLYGTFEMLSS
WRKTREDQHVKERTAAVYADSMLSFSLTTAMYLVTFGIGASPFTNIEAAR
IFCCNSCIAIFFNYLYVLSFYGSSLVFTGYIENNYQHSIFCRKVPKPEAL
QEKPAWYRFLLTARFSEDTAEGEEANTYESHLLVCFLKRYYCDWITNTYV
KPFVVLFYLIYISFALMGYLQVSEGSDLSNIVATATQTIEYTTAQQKYFS
NYSPVIGFYIYESIEYWNTSVQEDVLEYTKGFVRISWFESYLNYLRKLNV
STGLPKKNFTDMLRNSFLKAPQFSHFQEDIIFSKKYNDEVDVVASRMFLV
AKTMETNREELYDLLETLRRLSVTSKVKFIVFNPSFVYMDRYASSLGAPL
HNSCISALFLLFFSAFLVADSLINVWITLTVVSVEFGVIGFMTLWKVELD
CISVLCLIYGINYTIDNCAPMLSTFVLGKDFTRTKWVKNALEVHGVAILQ
SYLCYIVGLIPLAAVPSNLTCTLFRCLFLIAFVTFFHCFAILPVILTFLP
PSKKKRKEKKNPENREEIECVEMVDIDSTRVVDQITTV (SEQ ID NO: 18)

Figure 7B

BIOMARKERS FOR AUTISM SPECTRUM DISORDERS

FIELD OF THE INVENTION

The present invention relates to genetic markers for Autism Spectrum Disorders (ASD).

BACKGROUND OF THE INVENTION

Autism is a heritable neurodevelopmental condition characterized by impairments in social communication and by a preference for repetitive activities. Autism is not a distinct categorical disorder but is the prototype of a group of conditions defined as Pervasive Developmental Disorders (PDDs) or Autism Spectrum Disorders (ASD), which include Asperger's Disorder, Childhood Disintegrative Disorder, Pervasive developmental disorder-not otherwise specified (PDD-NOS) and Rett Syndrome. ASD is diagnosed in families of all racial, ethnic and social-economic backgrounds with incidence roughly four times higher in males compared to females. Overall population prevalence of autism has increased in recent years to a current estimate of 20 in 10,000 with incidence as high as 60 in 10,000 for all autism spectrum disorders.

Data from several epidemiological twin and family studies provide substantial evidence that autism has a significant and complex genetic etiology. The concordance rate in monozygotic twins is 60-90% (Bailey 1995), and the recurrence rate in siblings of affected probands has been reported to be between 5-10% (Jones & Szatmari 1988) representing a 50 fold increase in risk compared to the general population. Although autism spectrum disorders are among the most heritable complex disorders, the genetic risk is clearly not conferred in simple Mendelian fashion.

In a minority of cases (~10%), autism is part of a broader recognizable disorder (e.g. fragile X syndrome, tuberous sclerosis) or is associated with cytogenetically-detectable chromosome abnormalities. Moreover, co-morbidity of autism with microdeletion syndromes (e.g. William-Beuren and Sotos) and other genomic disorders (e.g. Prader-Willi/Angelman) suggests chromosomal imbalances are involved in the underlying etiology. The most frequent cytogenetic anomaly is an interstitial, maternally-inherited duplication of 15q11-13 (1-3%) encompassing the Prader Willi/Angelman Syndrome critical region. There are also a large number of cases with deletions in the q11.2 and q13.3 regions of chromosome 22. The 22q11.2 region is associated with velo-cardio-facial Syndrome and deletions at 22q13.3 appear to also represent a clinically definable syndrome. Both deletions are associated with the autistic phenotypes. Other chromosome loci associated with anomalies with a higher frequency of events observed in syndromic forms of ASD include 7q (see TCAG www.chr7.org), 2q37, 5p14-15, 17p11.2. In addition, reciprocal duplications overlapping the William-Beuren deletion region have been associated with the autism phenotype.

Genome-wide linkage scans have found evidence for susceptibility loci on almost all chromosomes with 7q yielding the most consistent results. Other loci with significant linkage include 2q (IMOSAC 2001), 3q and most recently 1lp (AGP 10K study). In some instances, like 7q, there is considerable overlap between cytogenetic anomalies and linkage results. However, the lack of linkage found at 15q11-13 and 22q13.3 loci reflect considerable heterogeneity in ASD and suggest that these rearrangements are responsible for a particular ASD subtype involving genes that do not contribute to the phenotype in cytogenetically normal patients. Despite promising results, no specific genes within these linkage peaks have unequivocally been shown to contribute to autism.

Mutations associated with ASD have been reported in two neuroligin (NLGN3 and NLGN4) genes and more recently SHANK3; however, these account for only rare causes of ASD. Other genes have been implicated, but represent rare events or have not yet been validated by other studies.

Together these data suggest substantial genetic heterogeneity with the most likely cause of non-syndromic idiopathic ASD involving multiple epistatically-interacting loci.

The identification of large scale copy number variants (CNVs) represents a considerable source of genetic variation in the human genome that contributes to phenotypic variation and disease susceptibility found small inherited deletions in autistic kindreds suggesting possible susceptibility loci.

It would be desirable to identify genetic markers of ASD that facilitate in a determination of the risk of ASD in an individual, as well as to assist in the diagnosis of the condition.

SUMMARY OF THE INVENTION

A number of genetic markers have now been identified which are useful in assessing the risk of ASD in an individual, as well as being useful to diagnose the condition. The markers are useful both individually and in the form of a microarray to screen individuals for risk of ASD.

Thus, in one aspect of the present invention, a method of determining the risk of ASD in an individual is provided comprising: probing a nucleic acid-containing sample obtained from the individual for a gene encoding PTCHD1, wherein a determination that the gene comprises a deletion of at least a portion of exon 1 is indicative of a risk of ASD in the individual.

In another aspect of the present invention, a method of determining the risk of ASD in an individual is provided comprising:

probing a nucleic acid-containing sample obtained from the individual for a mutation that modulates the expression of at least one gene selected from the group consisting of PTCHD1, SHANK3, NFIA, DPP6, DPP10, GPR98, PQBP1, ZNF41 and FTSJ1, wherein identification of a mutation that modulates the expression of at least one of said genes is indicative of a risk of ASD.

In another aspect of the invention, a method of determining the risk of ASD in an individual is provided comprising:

screening a biological sample obtained from the individual for abnormal levels of at least one gene product expressed by a gene selected from the group consisting of PTCHD1, SHANK3, NFIA, DPP6, DPP10, GPR98, PQBP1, ZNF41 and FTSJ1, wherein a determination that at least one of said gene products is expressed at a level that varies from the level in a healthy non-ASD individual is indicative of a risk of ASD.

In a further aspect of the invention, a method of determining the risk of ASD in an individual is provided comprising:

screening a nucleic acid-containing sample from the individual for genomic sequence variations that modulate the expression of PTCHD1.

These and other aspects of the present invention are described by reference to the following figures in which:

BRIEF DESCRIPTION OF THE DRAWINGS

FIG. 7A illustrates the cDNA sequence of the PTCHD1 gene; and FIG. 7B illustrates the corresponding amino acid sequence.

DETAILED DESCRIPTION OF THE INVENTION

Figure 1:
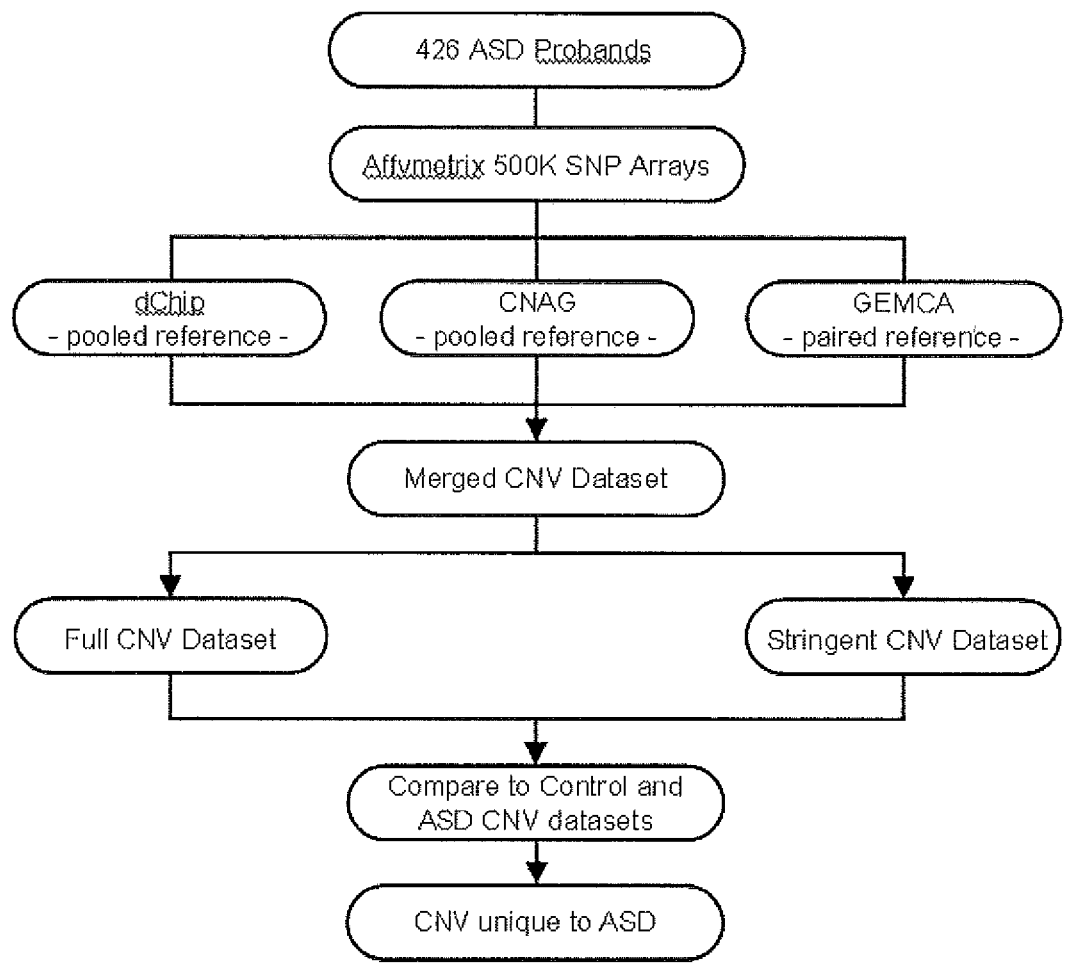
FIG. 1 is a flow chart depicting the methodology used to identify ASD-specific CNVs.

A method of determining the risk of an autism spectrum disorder (ASD) in an individual is provided comprising screening a biological sample obtained from the individual for a mutation that may modulate the expression of at least one gene selected from the group consisting of PTCHD1, SHANK3, NFIA, DPP6, DPP10, DPYD, GPR98, PQBP1, ZNF41 and FTSJ1. Such genes are referred to herein as "ASD-associated" genes.

The term "an autism spectrum disorder" or "an ASD" is used herein to refer to at least one condition that results in developmental delay of an individual such as autism, Asperger's Disorder, Childhood Disintegrative Disorder, Pervasive Developmental Disorder-Not Otherwise Specified (PDD-NOS) and Rett Syndrome (APA DSM-IV 2000).

In the present method of determining ASD risk in an individual, a biological sample obtained from the individual is utilized. A suitable biological sample may include, for example, a nucleic acid-containing sample or a protein-containing sample. Examples of suitable biological samples include saliva, urine, semen, other bodily fluids or secretions, epithelial cells, cheek cells, hair and the like. Although such non-invasively obtained biological samples are preferred for use in the present method, one of skill in the art will appreciate that invasively-obtained biological samples, may also be used in the method, including for example, blood, serum, bone marrow, cerebrospinal fluid (CSF) and tissue biopsies such as tissue from the cerebellum, spinal cord, prostate, stomach, uterus, small intestine and mammary gland samples. Techniques for the invasive process of obtaining such samples are known to those of skill in the art. The present method may also be utilized in prenatal testing for the risk of ASD using an appropriate biological sample such as amniotic fluid and chorionic villus.

In one aspect, the biological sample is screened for nucleic acid encoding selected genes in order to detect mutations associated with an ASD. It may be necessary, or preferable, to extract the nucleic acid from the biological sample prior to screening the sample. Methods of nucleic acid extraction are well-known to those of skill in the art and include chemical extraction techniques utilizing phenol-chloroform (Sambrook et al., 1989), guanidine-containing solutions, or CTAB-containing buffers. As well, as a matter of convenience, commercial DNA extraction kits are also widely available from laboratory reagent supply companies, including for example, the QIAamp DNA Blood Minikit available from QIAGEN (Chatsworth, Calif.), or the Extract-N-Amp blood kit available from Sigma (St. Louis, Mo.).

Once an appropriate nucleic acid sample is obtained, it is subjected to well-established methods of screening, such as those described in the specific examples that follow, to detect genetic mutations indicative of ASD, i.e. ASD-linked mutations. Mutations, such as genomic copy number variations (CNVs), which include gains and deletions of segments of DNA, for example, segments of DNA greater than about 1 kb, such as DNA segments between about 300 and 500 kb, as well as base pair mutations such as nonsense, missense and splice site mutations, including sequence mutations in both coding and regulatory regions of a gene, have been found to be indicative of ASD.

ASD-linked mutations such as CNVs are not restricted to a single chromosome, but rather have been detected on a multiple chromosomes such as the X chromosome, chromosome 15 and chromosome 21, and on various regions of the same chromosome such as at Xp11 and Xp22. Examples of CNVs that have been determined to be linked to ASD include a deletion on chromosome Xp22 including at least a portion of exon 1 of the PTCHD1 gene; a duplication on chromosome 15q11; and a deletion within the SHANK3 gene.

Genomic sequence variations of various types in different genes have been identified as indicative of ASD. CNVs in the DPP10 gene, including intronic gains, such as a 105 kb intronic gain, and exonic losses, such as a 478 kb exonic loss, both of which are more specifically identified in Table 1, have been identified; CNVs in the DPP6 gene, such as a 66 kb loss encompassing exons 2 and 3 and gains such as a CNV encompassing the entire DPP6 gene, a 270 kb exonic gain (exon 1), and a 16 kb intronic gain (see Table 1); CNVs in the SHANK3 gene such as a 276 kb loss; and CNVs in the DYPD gene such as a loss of the entire gene.

In one embodiment, genomic sequence variations that inhibit the expression of PTCHD1 have been linked to ASD. The terminology "inhibit expression" refers broadly to sequence variations that may inhibit, or at least reduce, any one of transcription and/or translation, as well as the activity of the PTCHD1 protein. For example, a CNV in the PTCHD1 gene comprising a large deletion of the coding region which results in at least a reduction of the expression of PTCHD1 protein has been found to be indicative of ASD. Although the CNV is not particularly restricted, the CNV deletion may include, for example, at least a portion of exon 1, but may additionally include surrounding regions as well, such as intron 1, in whole or in part, or a portion or more of the upstream region thereof.

Genomic sequence variations other than CNVs have also been found to be indicative of ASD, including, for example, missense mutations which result in amino acid changes in a protein that may also affect protein expression. In one embodiment, missense mutations in the PTCHD1 gene have been identified which are indicative of ASD, including missense mutations resulting in the following amino acid substitutions in the Ptchd1 protein: L73F, I173V, V195I, ML336-3371I and E479G.

To determine risk of ASD in an individual, it may be advantageous to screen for multiple genomic mutations, including CNVs and other mutations as indicated above applying array technology. In this regard, genomic sequencing and profiling, using well-established techniques as exemplified herein in the specific examples, may be conducted for an individual to be assessed with respect to ASD risk/diagnosis using a suitable biological sample obtained from the individual. Identification of one or more mutations associated with ASD would be indicative of a risk of ASD, or may be indicative of a diagnosis of ASD. This analysis may be conducted in combination with an evaluation of other characteristics of the individual being assessed, including for example, phenotypic characteristics.

In view of the determination of gene mutations which are linked to ASD, a method for determining risk of ASD in an individual is also provided in which the expression or activity of a product of an ASD-linked gene mutation is determined in a biological protein-containing sample obtained from the individual. Abnormal levels of the gene product or abnormal levels of the activity thereof, i.e. reduced or elevated levels, in comparison with levels that exist in healthy non-ASD individuals, are indicative of a risk of ASD, or may be indicative of ASD. Thus, a determination of the level and/or activity of the gene products of one or more of PTCHD1, SHANK3, NFIA, DPP6, DPP10, DYPD, GPR98, PQBP1, ZNF41 and FTSJ1, may be used to determine the risk of ASD in an individual, or to diagnose ASD. As one of skill in the art will appreciate, standard assays may be used to identify and quantify the presence and/or activity of a selected gene product.

Embodiments of the invention are described by reference to the following specific examples which is not to be construed as limiting.

Example 1

DNA Samples and Population Structure

The study included 426 ASD families. All of the index cases met Autism Diagnostic Interview-Revised (ADI-R) and Autism Diagnostic Observation Schedule (ADOS) criteria or on a clinical best estimate (Risi et al. J Am Acad Child Adolesc Psychiatry 2006; 45(9):1094-103). Thirty-two of these carried a cytogenetic chromosome rearrangement; 18 were detected by karyotyping 328 of 412 samples that originated from child diagnostic centres at the Hospital for Sick Children in Toronto and from St. John's, Newfoundland; 14 were already known to carry karyotypic anomalies (see Table 1 for information on these 32 patients). Affected and unaffected siblings were also assessed, and 56% (237/426) had one child (simplex) and 44% (189/426) had more than one child (multiplex) with ASD. Most cases were screened for fragile X mutations (75%) and if detected they were not included in the study. Most experiments were performed on blood genomic DNA (80%), otherwise the source was cell lines, e.g. lymphoblast cell lines. Population ancestry was estimated using STRUCTURE (Falush et al. Genetics 2003; 164(4):1567-87; Pritchard et al. Genetics 2000; 155(2):945-59).

TABLE 1

| | | Phenotype/Family | | Cytogenetic Analysis | | | CNV Analysis | | | | | | | |
|---|---|---|---|---|---|---|---|---|---|---|---|---|---|---|
| | | | | | Breakpoint | | | | | | | | | |
| | Sample ID | type | Karyotype | Location | RefSeq Genes | Chr | CNV | Size (bp) | Location | AS/Str[a] | RefSeq Genes | Comments | | |
| 1 | NA0008-000 (50863L) | Simplex family ASD, developmental dyspraxia | 46, XX, t(2;6)(q32;p22) unknown | 2q33.1: 200,096,682-200,154,790 | SATB2 | 2p11.2 | Loss | 917,200 | 89,056,400-89,973,600 | No/NS | No known genes | NFLD | | |
| | | | | 6p22.3: 21,561,566-21,644,040 | No known genes | 6p21.33 | Gain | 54,600 | 30,134,300-30,188,900 | Yes/NS | ZNRD1, PPP1R11, RNF39, TRIM31 SLC1A2 | | | |
| | | | | | | 11p13 | Gain | 54,200 | 35,332,700-35,386,900 | No/NS | No known genes | | | |
| | | | | | | 13q21.33 | Loss | 28,200 | 69,642,500-69,670,700 | No/NS | No known genes | | | |
| | | | | | | 14q11.2 | Gain | 549,300 | 21,490,300-22,039,600 | No/NS | No known genes | | | |
| | | | | | | 14q32.33 | Loss | 64,000 | 106,152,000-106,216,000 | No/NS | No known genes | | | |
| 2 | NA0005-000 (53601L) | Simplex family ASD, seizure disorder, obesity, macrocephaly | 46, XX, t(4;5)(q21;q13) unknown | 4q21.3 | Several | 1p13.2 | Gain | 128,963 | 112,783,876-112,912,839 | Yes/NS | ST7L, CAPZA1 | NFLD | | |
| | | | | | | 2q37.3 | Loss | 602,914 Error! Hyperlink reference not valid. | 242,127,468-242,730,382 | No/S | 10 genes | | | |
| | | | | 5q14.2-q14.3: 82,802,678-91,285,973 | Several | 3q29 | Loss | 43,033 | 196,922,636-196,965,669 | No/NS | MUC20, MUC4 | | | |
| | | | | | | 5q15 | Loss | 48,627 | 97,076,449-97,125,076 | No/NS | No known genes | | | |
| | | | | | | 5q21.3 | Loss | 13,000 | 109,391,000-109,404,000 | Yes/NS | No known genes | | | |
| | | | | | | 8p23.1 | Gain | 448,146 | 12,039,387-12,487,533 | No/S | FAM86B1, DEFB130, LOC440053 | | | |
| | | | | | | 14q11.2 | Gain | 223,579 | 19,272,965-19,496,544 | No/S | 6 OR genes | | | |
| | | | | | | 14q11.2 | Gain | 650,430 | 21,407,981-22,058,411 | No/S | No known genes | | | |
| | | | | | | 15q11.2 | Gain | 1,642,961 Error! Hyperlink reference not valid. | 18,446,422-20,089,383 | No/NS | LOC283755, POTE15, OR4M2, OR4N4 | | | |
| 3 | NA0039-000 (69736) | Simplex family ASD, submucous cleft, globally developmentally delayed, large ears, short forehead, | 46, XX, der(22)t(14;22)(q32;q13) pat inherited | See CNV | See CNV | 9q32 | Gain | 498,000 | 114,038,000-114,536,000 | No/NS | 7 genes | NFLD Unaffected sibling with ADHD has 46, XX, der(14) t(14;22)(q32;q13) | | |
| | | | | | | 14q32.33 | Gain | 1,436,000 | 104,920,000-106,356,000 | No/NS | 6 genes | | | |
| | | | | | | 15q13.3 | Gain | 502,500 | 29,796,300-30,298,800 | No/NS | CHRNA7 | | | |

TABLE 1-continued

| Sample ID | Phenotype/Family type | Cytogenetic Analysis | | | CNV Analysis | | | | | | Comments |
|---|---|---|---|---|---|---|---|---|---|---|---|
| | | Karyotype | Breakpoint Location | RefSeq Genes | Chr | CNV | Size (bp) | Location | AS/Str[a] | RefSeq Genes | |
| | distally tapere fingers, severe pea planovalgus | | | | 22q13.31-q31.33 | Loss | 3,231,700 | 46,277,400-49,509,100 | Yes/NS | 40 genes + SHANK3 | SK |
| 4 SK0283-003 (72309) | Simplex family ASD | 47, XX, ring chromosome 1 de novo | See CNV | See CNV | 1p22.3 | Gain | 23,993 | 87,417,351-87,441,344 | Yes/NS | No known genes | SK |
| | | | | | 1q21.2-q21.3 | Gain | 1,451,926 | 148,095,537-149,547,463 | Yes/S | 36 genes | |
| | | | | | 3p26.1 | Loss | 44,458 | 5,365,506-5,409,964 | Yes/S | No known genes | |
| | | | | | 4p13 | Gain | 95,508 | 44,762,996-44,858,504 | Yes/S | No known genes | |
| | | | | | 4q33 | Loss | 82,224 | 171,715,627-171,797,851 | Yes/NS | No known genes | |
| | | | | | 5q31.3 | Loss | 355,649 | 140,656,658-141,014,307 | Yes/NS | 8 genes | |
| | | | | | 6p12.3 | Gain | 13,950 | 46,962,122-46,976,072 | No/NS | GPR116 | |
| | | | | | 7p14.1 | Loss | 102,939 | 38,041,635-38,144,574 | No/NS | STARD3NL, TARP | |
| | | | | | 7q34 | Loss | 169,191 | 141,813,948-141,983,139 | No/NS | PRSS1 | |
| | | | | | 14q11.2 | Loss | 583,148 | 21,455,546-22,038,694 | No/S | No known genes | |
| | | | | | 15q11.2 | Loss | 1,632,769 | 18,427,103-20,059,872 | No/S | LOC283755, POTE15, OR4M2, OR4N4 | |
| | | | | | 17q21.31 | Loss | 140,746 | 41,570,665-41,711,411 | No/NS | KIAA1267 | |
| 5 SK0044-003 (50067) | Simplex family ASD | 46, XY, t(1;2)(p22.1;p23)pat der(13;15)(q10;q10)mat inherited | 1p31.1: 72,065,578-72,153,007; 2p24.3: 12,376,807-12,733,637; 13q10: in progress; 15q10: in progress | NEGR1 | 7p14.1 | Gain | 85,900 | 39,828,000-39,913,900 | No/NS | CDC2L5 | SK |
| 6 SK0182-003 (52065) | Simplex family ASD | 46 XY, t(1;9)(q25;p13) inherited | 1q24.2: 167,452,268-167,522,136; 9p12: 45,695,701-45,737,008 | No known genes | 2p24.3 | Gain | 15,100 | 14,304,500-14,319,600 | No/NS | No known genes | SK Younger brother has the same translocation and severe speech and language disorder but does not meet ASD criteria on ADOS. |
| | | | | No known genes | 14q11.2 | Gain | 288,100 | 19,204,300-19,492,400 | No/S | 6 genes | |

TABLE 1-continued

| Sample ID | Phenotype/Family type | Cytogenetic Analysis Karyotype | Breakpoint Location | RefSeq Genes | Chr | CNV | Size (bp) | CNV Analysis Location | AS/Str[a] | RefSeq Genes | Comments |
|---|---|---|---|---|---|---|---|---|---|---|---|
| 7 SK0335-003 (72815) | Simplex Family ASD, mental retardation | 46, XXX, t(2:10)(q22:q22.3) unknown | 2q23.1: 148,936,284-149,125,547 10q23.31: 91,265,490-91,461,660 | LOC401431, ATP6VOE2 SLC16A12, PANK1, MPHOSPH1 | 2p13.3 | Gain | 374,900 | 70,152,900-70,527,800 | Yes/NS | 6 genes | Others Non-Canadian family |
| | | | | | 3q29 | Gain | 43,033 | 196,922,636-196,965,669 | No/NS | MUC20, MUC4 | |
| | | | | | 5p13.1 | Loss | 272,618 | 38,534,384-38,807,002 | Yes/S | LIFR | |
| | | | | | 6p21.32 | Gain | 162,900 | 32,344,099-32,506,999 | Yes/NS | C6orf10, BTNL2 | |
| | | | | | 8p23.1 | Gain | 21,783 | 12,264,620-12,286,403 | No/NS | No known genes | |
| | | | | | 9q32 | Gain | 22,000 | 114,153,000-114,175,000 | No/S | ORM1, ORM2 | |
| | | | | | 14q11.2 | Gain | 331,503 | 21,717,112-22,048,615 | No/S | No known genes | |
| | | | | | 15q11.2 | Gain | 1,516,085 | 18,427,100-19,943,185 | No/S | LOC283755, POTE15, OR4M2, OR4N4 | |
| | | | | | 16p11.2-11.1 | Gain | 266,336 | 34,325,041-34,591,377 | No/NS | No known genes | |
| | | | | | 17q21.31 | Gain | 201,731 | 41,518,102-41,719,833 | No/S | KIAA1267 | |
| | | | | | 20p12.1 | Loss | 27,500 | 14,973,800-15,001,300 | Yes/S | C20orf133 | |
| 8 SK0125-003 (59144) | Multiplex family ASD | 46, XY, t(2:11)(p11.2:q13.3) pat inherited | 2p11.2: 89,117,655-89,158,494 11q13.1: 64,821,333-64,861,285 | No known genes POLA2, CDC42EP2, DPF2 | 2q34 | Loss | 3,000 | 213,013,000-213,016,000 | Yes/NS | ERBB4 | Other Canadian Family |
| 9 SK0152-003 (41548L) | Multiplex family ASD, oral motor apraxia, poor balance and coordination, mild hypotonia, walks with a wide gait, severe language delay, moderate intellectual disability, some facial features of Cri du Chat | 46, XY, inv(3)(p24:q24), t(5:7)(p15:p13) de novo | 3p24: not available 3q24: not available 5p14.3: 19,825,926-19,883,410 7p13: 46,618,434-48,733,542 | CDH18 No known genes | 3p25.1-p24.3 | Loss | 1,409,600 | 15,125,800-16,535,400 | Yes/S | 12 genes | Other Canadian Family Previously described in a manuscript by Harvard et al. The 3p25.1, 5p15.31-p15.2 and 18q12.2 deletions were identified in Harvard, C. et al using BAC CGH. The deletion size has been refined here using SNPs. Older sibling also |
| | | | | | 3p12.3 | Gain | 55,000 | 78,902,000-78,957,000 | Yes/S | ROBO1 | |
| | | | | | 5p15.31-p15.2 | Loss | 3,429,389 | 9,275,811-12,705,200 | Yes/S | 8 genes | |
| | | | | | 6q16.1 | Loss | 60,058 | 95,556,287-95,616,345 | No/S | No known genes | |
| | | | | | 7p14.1 | Gain | 35,243 | 38,096,725-38,131,968 | No/NS | No known genes | |
| | | | | | 10q11.22 | Gain | 455,130 | 47,030,119-47,485,249 | No/S | ANXA8 | |
| | | | | | 12p11.21 | Gain | 63,728 | 31,904,362-31,968,090 | No/S | No known genes | |
| | | | | | 12q12 | Loss | 422,842 | 40,584,198-41,007,040 | Yes/S | YAF2, ZCRB1 | |

TABLE 1-continued

| Sample ID | Phenotype/Family type | Cytogenetic Analysis - Karyotype | Breakpoint Location | RefSeq Genes | CNV | Size (bp) | CNV Analysis - Location | Chr | AS/Str[a] | RefSeq Genes | Comments |
|---|---|---|---|---|---|---|---|---|---|---|---|
| | | | | | Gain | 491,397 | 21,584,229-22,075,626 | 14q11.2 | No/S | No known genes | has ASD but has a normal 46,XX karyotype |
| | | | | | Gain | 22,269 | 106,223,861-106,246,130 | 14q32.33 | No/NS | No known genes | Maternal aunt with schizophrenia and a maternal uncle with Down syndrome |
| | | | | | Loss | 1,632,718 | 18,446,422-20,079,140 | 15q11.2 | No/S | LOC283755, POTE15, OR4M2, OR4N4 | |
| | | | | | Loss | 91,432 | 63,768,909-83,860,341 | 16q21 | Yes/NS | No known genes | |
| | | | | | Gain | 219,797 | 41,500,036-41,719,833 | 17q21.31 | No/NS | KIAA1267 | |
| | | | | | Loss | 816,914 | 32,174,061-32,990,975 | 18q12.2 | Yes/S | KIAA1328, C18orf10, FMOD3 | |
| 10 SK0105-003 (27155L) | Multiplex family ASD, primarily non-verbal, profound developmental delay | 46,XY, inv(4)(p12:p15.3) inherited | 4p15.3: 12,173,445-12,335,572 | No known genes | Gain | 1,098,400 | 41,956,500-43,054,900 | 10q11.21 | Yes/NS | RET, RASGEF1A, BMS1L, ZNF11B, MGC16291, GALNACT-2 | SK Described previously in Vincent et al.[2] Affected brother, apparently unaffected mother and unaffected maternal grandfather all have the same inversion. Distal 4p15.3 breakpoint maps ~12 Mb to a region previously indicated to show linkage to autism. |
| | | | 4p12: 44,876,353-46,024,488 | GABRG1 (breakpoint region is located in inbom 7) | Gain | 162,300 | 47,414,800-47,577,100 | 13q14.2 | Yes/NS | MED4, NUDT15, SUCL42 | |
| | | | | | Loss | 56,600 | 61,854,900-61,911,500 | 16q21 | Yes/NS | No known genes | |
| | | | | | Gain | 238,600 | 41,521,600-41,760,200 | 17q21.31 | No/NS | KIAA1267 | |
| 11 SK0205-004 (56242) | Simplex family ASD | 46, XX, del(5)(p15.1) de novo | See CNV | See CNV | Gain | 96,068 | 199,226,000-199,322,068 | 3q29 | No/NS | LMLN, LOC348840 | SK FISH analysis with subtelomeric probe (containing D5S2488) was consistent with a terminal deletion on 5p. |
| | | | | | Loss | 13,800,984 | 81,949-13,882,933 | 5p15.33-p15.2 | Yes/S | >50 genes | |
| | | | | | Loss | 70,891 | 97,054,185-97,125,076 | 5q15 | No/NS | No known genes | |
| | | | | | Gain | 1,121,866 | 46,363,383-47,485,249 | 10q11.22 | No/S | SYT15, ANXA6, ANXA8L1, PPYR1, GPRIN2 | |
| | | | | | Loss | 29,732 | 67,747,770-67,777,502 | 10q21.3 | No/NS | CTNNA3 | |
| | | | | | Gain | 244,432 | 135,079,000-135,323,432 | 10q26.3 | No/S | SYCE1; CYP2E1 | |

TABLE 1-continued

| Sample ID | Phenotype/Family type | Cytogenetic Analysis Karyotype | Breakpoint Location | RefSeq Genes | Chr | CNV | Size (bp) | CNV Analysis Location | AS/Str[a] | RefSeq Genes | Comments |
|---|---|---|---|---|---|---|---|---|---|---|---|
| | | | | | 14q11.2 | Gain | 217,035 | 19,272,965-19,490,000 | No/S | OR4K1, OR4N2, OR4K5, OR4K2 | |
| | | | | | 15q11.2 | Gain | 1,662,300 | 18,427,100-20,089,400 | No/S | LOC283755, POTE15, OR4M2, OR4N4 | |
| | | | | | 17q21.31 | Gain | 65,845 | 41,006,823-41,072,668 | No/S | No known genes | |
| | | | | | 17q21.31 | Gain | 187,028 | 41,521,621-41,708,649 | No/NS | KIAA1267 | |
| | | | | | 22q11.21 | Gain | 150,753 | 17,265,500-17,416,253 | No/S | DGCR6, PRODH, DGCR2 | |
| 12 SK0061-003 (44951) | Simplex family ASD, developmental delay | 46, XY, t(5:7)(q15:q31.32) unknown | 7q31.31: 118,928,065-119,006,076 5q14.3: 88,849,193-88,891,151 | No known genes  No known genes | | | | No CNV detected | | | Other Non-Canadian Family |
| 13 SK0195-003 (55310) | Simplex family ASD | 46, XY, t(5:8:17)(q31.1:q24.1:q21.3) de novo | 5q31.1: 136,979,583-137,038,092 8q24.22: 132,448,049-132,512,973 17q21.31: 41,893,216-42,093,636 | KLHL3  No known genes  LRRC37A2, ARL17P1, LOC641522, NSF | 2p16.1 | Gain | 47,900 | 57,314,000-57,361,900 | No/NS | No known genes | Other Canadian Family |
| | | | | | 10q23.1 | Loss | 17,500 | 83,772,000-83,789,500 | Yes/NS | NRG | |
| | | | | | 14q11.2 | Gain | 288,100 | 19,204,300-19,492,400 | No/NS | OR4K1, OR4N2, OR4M1, OR4K5, OR4Q3, OR4K2 | |
| | | | | | 17q21.31 | Gain | 644,700 | 41,521,600-42,166,300 | No/S | KIAA1267 | |
| 14 SK0133-003 (46012) | Simplex family ASD | 46, XY, t(6:7)p11.2q22)pat inherited | 6p12.1: 56,805,919-56,967,398 7q22.1: 97,933,646-97,973,368 | DST, c6orf65  No known genes | 2q37.1 | Gain | 314,000 | 232,076,000-232,390,000 | Yes/NS | MGC43122, NMUR1, MGC35154, NCL, B3GNT7 | Other Canadian Family CNV seen at 11q25 is in the same breakpoint region as Sample SK0145-003 |
| | | | | | 5q14.3 | Gain | 633,400 | 89,492,800-90,126,200 | Yes/NS | CETN3, LOC153364, POLR3G, MASS1 | |
| | | | | | 7q33 | Loss | 3,000 | 136,255,000-136,258,000 | No/NS | No known genes | |
| | | | | | 8q23.2 | Loss | 32,000 | 111,182,000-111,214,000 | No/NS | No known genes | |
| | | | | | 9p21.3 | Loss | 8,200 | 25,073,909-25,982,109 | Yes/NS | No known genes | |
| | | | | | 11q25 | Gain | 369,090 | 133,855,000-134,224,000 | No/S | No known genes | |
| | | | | | 12q21.33 | Gain | 19,700 | 90,807,700-90,827,400 | Yes/NS | No known genes | |
| | | | | | 13q21.32 | Loss | 2,500 | 65,576,300- | Yes/NS | No known genes | |

TABLE 1-continued

| | Sample ID | Phenotype/Family type | Cytogenetic Analysis | | | CNV Analysis | | | | | | |
|---|---|---|---|---|---|---|---|---|---|---|---|---|
| | | | Karyotype | Breakpoint Location | RefSeq Genes | Chr | CNV | Size (bp) | Location | AS/Str[a] | RefSeq Genes | Comments |
| 15 | SK0043-003 (29346) | Multiplex family ASD | 46, XY, t(6:9)(q10:q12) unknown | 6q11.2-q12: 63,464,452-63,511,410 9q21.1: 66,599,032-68,682,365 | No known genes PIP5K1B | 8p23.2 15q11.2 | Loss Gain | 35,040 1,713,200 | 65,578,800 3,984,190-4,019,230 18,376,200-20,089,400 | No/NS No/S | CSMD1 LOC283755, POTE15, OR4M2, OR4N4 | SK Sibling also has ASD but a normal 45, XY karyotype |
| 16 | SK0181-004 (52191) | Simplex family ASD | 46, XY, t(6:14)(q13:q21) de novo | 6q12: 69,241,818-69,279,457 14q21.1-q21.2: 40,807,716-44,806,460 | No known genes LRFN5, c14orf155, c14orf28, BTBD5, KIAA0423, PRPF39, FKBP3, AK093422, KIAA1596, FANCM, c14orf106 | 3p14.1-p13 4q28.3 | Loss Loss | 5,346,900 254,000 | 65,286,300-70,633,200 135,282,000-135,536,000 | Yes/S No/NS | 13 genes No known genes | SK |
| 17 | SK0083-003 (50800L) | Simplex family ASD, craniosynostosis, developmental verbal dyspraxia, motor delay | 46, XY, del(7)(q31.1q31.32) de novo | 7q31.1: 108,272,363-108,337,904 7q31.31: 119,007,999-119,335,246 | IMMP2L, LRRN3, DOCK4, ZNF277P, IFRD1 . . . to . . . ASZ1, CFTR, CTTNBP2, LSM8, ANKRD7 | 1q31.1 2p23.3 4q35.2 6p24.2 7q31.1-q31.31 7q36.2 8q24.21 10p11.23 14q11.2 17q21.31 | Loss Gain Gain Gain Loss Loss Gain Gain Loss Loss | 15,000 26,300 21,314 188,500 11,023,506 26,297 48,000 26,700 219,458 117,521 | 186,702,000-186,717,000 25,138,000-25,164,300 188,232,000-188,253,314 11,479,600-11,668,100 108,200,381-119,223,887 152,027,450-152,053,747 127,951,000-127,999,000 30,893,400-30,920,100 19,272,965-19,492,423 40,897,617-41,015,138 | No/S Yes/NS Yes/S Yes/NS Yes/S Yes/NS Yes/NS Yes/NS No/S No/NS | No known genes No known genes No known genes No known genes >50 genes No known genes No known genes No known genes OR4K1, OR4N2, OR4M1, OR4K5, OR4Q3, OR4K2 PLEKHM1 | Other Canadian Family Described previously in Feuk et al.[3] |
| 18 | SK0131-003 (39989) | Simplex family Autistic features, speech-language disorder (developmental verbal dyspraxia), dysmorphic features, mild developmental delay, unable to | 46, XX, del(7)(q31.2q32.2)(D7S486-D7S522-) de novo, WBS inv-2 de novo | 7q31.1: 113,181,975-113,518,235 7q32.2: 128,540,690-128,796,716 | FOXP2, MDFIC, TFEC, TES, CAV2, CAV1 . . . to . . . IRF5, TNPO3, TSPAN39, SMO, FAM40B, KIAA0828 | 2p22.2 3p21.31 4q31.21 7p14.1 7q31.1- | Gain Gain Gain Gain Loss | 67,740 52,599 120,171 147,076 15,486,721 | 37,848,232-37,915,972 147,754,068-147,806,667 145,146,000-145,266,171 38,096,725-38,243,801 113,335,000- | No/NS Yes/S No/S No/NS Yes/S | No known genes CCR5, CCRL2, CCR2 GYPE AMPH >50 genes | Other Canadian Family Described previously in Feuk et al.[3] |

TABLE 1-continued

| Sample ID | Phenotype/Family type | Cytogenetic Analysis | | | CNV Analysis | | | | | |
|---|---|---|---|---|---|---|---|---|---|---|
| | | Karyotype | Breakpoint Location | RefSeq Genes | Chr | CNV | Size (bp) | Location | AS/Str[a] | RefSeq Genes | Comments |
| | cough/sneeze/laugh spontaneously | | | | q32.2 8q13.3 | Gain | 261,985 | 128,821,721 72,881,221- 73,143,206 | Yes/NS | MSC, TRPA1 | |
| | | | | | 10q11.22 | Gain | 455,100 | 47,030,100- 47,485,200 | No/NS | ANXA8 | |
| | | | | | 10q26.2 | Gain | 91,077 | 128,501,014- 128,592,091 | Yes/S | DOCK1 | |
| | | | | | 13q21.33 | Loss | 44,235 | 69,634,055- 69,678,300 | No/NS | No known genes | |
| | | | | | 14q11.2 | Loss | 222,786 | 19,272,965- 19,495,751 | No/NS | OR4K1, OR4N2, OR4M1, OR4K5, OR4Q3, OR4K2 | |
| | | | | | 14q11.2 | Gain | 637,249 | 21,462,466- 22,099,715 | No/S | No known genes | |
| | | | | | 15q11.2 | Gain | 1,662,280 | 18,427,103- 20,089,383 | No/NS | LOC283755, POTE15, OR4M2, OR4N4 | |
| | | | | | 17q12 | Gain | 29,984 | 31,471,515- 31,501,499 | No/NS | No known genes | |
| | | | | | 22q11.22 | Gain | 810,876 | 20,772,047- 21,582,923 | No/NS | 6 genes | |
| 19 SK0002- 003 (50002) | Simplex family ASD, psychosis | 46, XX, inv(7)(p15.3:q22.1) unknown | 7p21.1: 18,284,397- 18,302,387 | No known genes | 4q28.3 | Gain | 765,000 | 132,195,000- 132,960,000 | No/S | No known genes | Other Non Canadian-Family |
| | | | 7q22.3: 104,360,659- 104,549,945 | SPRK2 | 5p15.1- 15.2 | Gain | 239,100 | 14,940,400- 15,179,500 | No/S | No known genes | |
| | | | | | 15q11.2 | Gain | 1,713,200 | 18,376,200- 20,089,400 | Yes/S | LOC283755, POTE15, OR4M2, OR4N4 | |
| 20 SK0211- 003 (58892) | Simplex family ASD, mild elevation of lactate | 46, XX, inv(7)(q22q34)mat inherited | 7q21.3: 96,943,657- 96,985,663 | No known genes | 7q22.1 | Gain | 379,000 | 100,393,000- 100,772,000 | No/NS | 10 genes | Other Non Canadian Family |
| | | | 7q34: 140,920,721- 140,958,207 | TAS2R4, TAS2R5 | 9p21.1 | Loss | 135,100 | 30,408,400- 30,543,500 | No/NS | No known genes | Mother and unaffected twin sister have the same karyotype: 7q34 breakpoint overlaps with a ASD translocation patient |
| 21 SK0040- 003 (55449) | Multiplex family ASD, ADHD, severe anxiety attacks, seizures, difficulties with fine and gross motor skills | 46, XY, t(7:8)(p15:q22), t(10:11)(q26:q23) unknown | 7p15.3: 21,825,126- 21,869,196 | No known genes | 2q37.3 | Loss | 95,959 | 242,634,423- 242,730,382 | No/S | No known genes | Other Non-Canadian Family |
| | | | 8q22.2: 99,652,299- 99,823,618 | STK3 | 10q21.3 | Loss | 144,903 | 67,734,600- 67,879,503 | No/S | CTNNA3 | Unaffected sister with normal female karyotype, has difficulties in |
| | | | | | 11q22.3 | Loss | 62,995 | 104,729,456- 104,792,451 | No/NS | No known genes | |

TABLE 1-continued

| Sample ID | Phenotype/Family type | Cytogenetic Analysis Karyotype | Breakpoint Location | RefSeq Genes | Chr | CNV | Size (bp) | CNV Analysis Location | AS/Str[a] | RefSeq Genes | Comments |
|---|---|---|---|---|---|---|---|---|---|---|---|
| | | | | | 14q11.2 | Gain | 219,458 | 19,272,965-19,492,423 | No/NS | OR4K2, OR4N2, OR4K1, OR4K5 | some muscles, difficulties with fine and gross motor skills, severe anxiety attacks, not able to relate to peers and is affected by noise |
| | | | | | 14q11.2 | Gain | 224,329 | 21,784,072-22,008,401 | No/NS | No known genes | |
| | | | | | 15q11.2 | Gain | 1,662,280 | 18,427,103-20,089,383 | No/S | LOC283755, POTE15, OR4M2, OR4N4 | |
| | | | | | 22q11.22 | Loss | 515,645 | 21,031,117-21,546,762 | No/NS | PRAME, SUHW2, SUHW1, GGTL4 | |
| | | | | | 22q11.23 | Gain | 269,129 | 23,975,202-24,244,331 | No/S | CTA, LRP5L | |
| 22 SK0145-003 (67955) | Simplex family ASD | 46, XX, t(7:11)(q31:q25)mat inherited | 7q31.2: 114,573,150-114,611,613 | No known genes | 1p36.11 | Gain | 192,600 | 26,231,500-26,424,100 | Yes/NS | 8 genes | Other Canadian Family Apparently unaffected mother has the same 7q31.2 and 11q25 breakpoints |
| | | | 11q25: 133,862,647-134,001,155 | No known genes | 2p24.2 | Gain | 14,233 | 17,416,366-17,430,599 | Yes/NS | No known genes | |
| | | | | | 3p23 | Gain | 26,509 | 34,844,620-34,873,129 | Yes/NS | No known genes | |
| | | | | | 5p15.33 | Gain | 3,029,476 | 165,712-3,195,188 | Yes/NS | 28 genes | |
| | | | | | 6p22.2 | Gain | 25,841 | 25,576,804-25,602,645 | Yes/NS | LRRC16 | |
| | | | | | 7p14.1 | Gain | 20,412 | 37,494,999-37,515,411 | No/NS | No known genes | |
| | | | | | 8q13.3 | Gain | 28,933 | 72,911,162-72,940,095 | Yes/NS | MSC | |
| | | | | | 10p12.1 | Loss | 68,961 | 27,642,965-27,741,926 | No/S | PTCHD3 | |
| | | | | | 12p123 | Gain | 37,831 | 18,855,833-18,893,664 | No/NS | No known genes | |
| | | | | | 14q11.2 | Gain | 464,929 | 21,551,291-22,016,220 | No/NS | No known genes | |
| | | | | | 15q23-24.1 | Gain | 435,603 | 70,053,228-70,486,831 | Yes/NS | 9 genes | |
| | | | | | 19q13.43 | Gain | 308,600 | 63,476,500-63,785,100 | Yes/NS | 18 genes | |
| 23 SK0031-003 (68160L) | Simplex family ASD, very little language, global developmental delays | 46, XY, t(7:13)(q31.3:q21) mat inherited | 7q31.2: 116,270,156-116,458,896 | ST7 | 5p13.2 | Loss | 3,000 | 36,495,800-36,498,800 | Yes/NS | No known genes | Other Non Canadian Family |
| | | | 13q21.1: 54,559,087-54,739,454 | No known genes | 6p22.1-21.33 | Gain | 79,600 | 29,967,200-30,046,800 | No/NS | HLA-A | |
| | | | | | 9p23 | Loss | 112,800 | 11,895,600-12,008,400 | No/NS | No known genes | |
| | | | | | 14q32.2 | Gain | 772,400 | 99,015,100-99,787,500 | Yes/S | 8 genes | |
| | | | | | 15q11.2 | Gain | 1,378,000 | 18,711,400-20,089,400 | No/S | LOC283755, POTE15, OR4M2, OR4N4 | |

TABLE 1-continued

| Sample | | | Cytogenetic Analysis | | | CNV Analysis | | | | | |
|---|---|---|---|---|---|---|---|---|---|---|---|
| | | | Breakpoint | | | | | | | | |
| ID | Phenotype/Family type | Karyotype | Location | RefSeq Genes | Chr | CNV | Size (bp) | Location | AS/Str[a] | RefSeq Genes | Comments |
| | | | | | 17q21.31 | Gain | 597,300 | 41,569,000-42,166,300 | No/NS | 6 genes | |
| | | | | | 22q11.23 | Gain | 251,200 | 23,989,900-24,240,200 | No/S | CTA-246H3.1, LRP5L | SK |
| 24 SK0073-003 (57283L) | Simplex family ASD, developmental delay, delayed expressive and receptive language | 47, XX, idic(15)(q13) de novo | 15q13: 26,918,525-31,848,963 | LOC400968, LOC283755, POTE15, OR4M2, OR4N4 . . . to . . . ARHGAP11A, c15orf45, GREM1, RYR3 | 1q25.2 | Gain | 424,000 | 176,522,000-176,946,000 | Yes/NS | 6 genes | Described previously in Kwasnicka-Crawford et al.[4] |
| | | | | | 2p23.3 | Gain | 703,500 | 24,701,300-25,404,600 | Yes/NS | 7 genes | |
| | | | | | 4p16.3 | Gain | 997,460 | 1,692,240-2,689,700 | Yes/NS | 12 genes | |
| | | | | | 4q35.1 | Gain | 311,000 | 185,856,000-186,167,000 | Yes/NS | CASP3, CCDC111, MLF1IP, ACSL1 | |
| | | | | | 5q31.1 | Gain | 93,000 | 134,426,000-134,519,000 | Yes/S | No known genes | |
| | | | | | 9p21.1 | Loss | 362,900 | 30,452,800-30,815,700 | No/NS | No known genes | |
| | | | | | 14q11.2 | Gain | 414,9090 | 21,660,700-22,075,600 | No/NS | No known genes | |
| | | | | | 15q11.2-13.3 | Gain | 11,922,600 | 18,376,200-30,298,890 | Yes/S | >50 genes | |
| | | | | | 16p11.2 | Gain | 1,543,900 | 28,062,200-29,606,100 | No/NS | >20 genes | |
| | | | | | 16p11.2 | Gain | 658,600 | 30,589,900-31,248,500 | No/NS | >20 genes | |
| 25 SK0218-003 (60340) | Multiplex family ASD, cleft palate, club feet, mild-facial hypoplasia, heart defect | 46, XX, del(18)(q21) de novo | 18q21.32: 55,690,398-55,884,029 | See CNV | 12p13.33 | Loss | 92,328 | 1,760,054-1,852,412 | Yes/S | CACNA2D4, ADIPOR2, LRTM2 | SK |
| | | | | | 15q11.2 | Loss | 1,613,450 | 18,446,422-20,059,872 | No/S | LOC283755, POTE15, OR4M2, OR4N4 | As noted in the Autism Chromosome Rearrangement Database there are 5 addition reported cases of abnormalities involving 18q: Sibling has a normal 46, XY karyotype also is affected with autism and has oromotor difficulties. |
| | | | | | 17q21.31 | Gain | 190,234 | 41,516,415-41,708,649 | No/NS | KIAA1267 | |
| | | | | | 18q21.32-q23 | Loss | 20,358,999 | 55,758,601-76,115,600 | Yes/S | >50 genes | |
| | | | | | 19q13.42 | Loss | 68,786 | 59,971,717-60,040,503 | No/NS | KIR3DP1, KIR2DL1, KIR3DL1, KIR2DL4, KIR2DS4 | |
| | | | | | 20p11.23 | Gain | 128,457 | 19,740,012-19,868,469 | Yes/NS | RIN2 | |
| 26 SK0215- | Simplex family | 46, XY, | 19p13.2: | EVI5L, FLJ22184, | 1p21.3 | Loss | 1,092,500 | 97,271,600- | Yes/S | FLJ35409, DPYD | Other |

TABLE 1-continued

| Sample ID | Phenotype/Family type | Cytogenetic Analysis Karyotype | Breakpoint Location | RefSeq Genes | CNV Analysis Chr | CNV | Size (bp) | Location | AS/Str[a] | RefSeq Genes | Comments |
|---|---|---|---|---|---|---|---|---|---|---|---|
| 006 (58449) | ASD | t(19;21)(p13.2:q22.12) inherited | 7,804,294-7,896,711 21q22.12: 36,091,999-36,191,098 | LRRC8E, MAP2K7, SNAPC2, CTXN1 No known genes | | | | 98,364,100 | | | Canadian Family Patient has an unaffected sister with the same karyotype |
| 27 SK0136-003 (51253) | Simplex family ASD | 46, X, der(Y)t(Y:15)(q12;p11.2) pat inherited | Not available | | 17p11.1-p11.2 | Gain | 503,100 | 21,634,900-22,138,000 | Yes/NS | FAM27L | SK |
| | | | | | 4p13 | Gain | 42,400 | 44,809,500-44,851,990 | No/NS | No known genes | |
| | | | | | 8p23.2 | Gain | 234,580 | 2,335,310-2,569,890 | No/NS | No known genes | |
| | | | | | 8q24.23 | Loss | 138,000 | 137,757,000-137,895,900 | No/NS | No known genes | |
| | | | | | 10p12.1 | Loss | 51,400 | 27,690,500-27,741,900 | No/NS | PTCHD3 | |
| | | | | | 15q11.2 | Loss | 558,300 | 18,676,700-19,235,000 | No/NS | LOC283755 | |
| | | | | | 15q26.3 | Gain | 386,100 | 99,827,900-100,216,000 | No/NS | PCSK6, TARSL2, TM2D3, OR4F6 | |
| 28 SK0243-003 (67941) | Simplex Family ASD | 46, XY, del(15)(q23q24.2) de novo | See CNV | See CNV | 1q21.1 | Loss | 333,539 | 145,700,996-146,034,535 | No/NS | No known genes | SK |
| | | | | | 2p22.2 | Gain | 52,951 | 37,847,789-37,900,740 | No/NS | No known genes | |
| | | | | | 3q27.3 | Gain | 91,422 | 187,897,578-187,989,000 | No/S | KNG1, EIF4A2 | |
| | | | | | 7p22.3 | Gain | 29,778 | 141,322-171,100 | No/NS | No known genes | |
| | | | | | 7p14.1 | Loss | 32,836 | 38,092,579-38,125,215 | No/NS | No known genes | |
| | | | | | 10p13 | Loss | 1,570 | 13,096,593-13,098,163 | No/NS | No known genes | |
| | | | | | 11p15.1 | Gain | 21,766 | 16,905,796-18,927,562 | No/NS | MRGPRX1 | |
| | | | | | 15q23-q24.2 | Loss | 4,289,500 | 69,601,300-73,890,800 | Yes/S | 55 genes | |
| | | | | | 17q12 | Gain | 38,247 | 31,483,252-31,501,499 | No/NS | No known genes | |
| | | | | | 17q21.31 | Gain | 83,359 | 41,636,474-41,719,833 | No/NS | No known genes | |
| 29 SK0245-005 (68517) | Simplex Family ASD, epicanthal folds, drooping eyes | 46, XY, trp(15)(q11.2q13) de novo | See CNV | See CNV | 6q14.1 | Loss | 47,288 | 79,036,117-79,083,405 | No/NS | No known genes | SK |
| | | | | | 7p14.1 | Loss | 57,861 | 38,067,354-38,125,215 | No/NS | No known genes | |
| | | | | | 10p13 | Loss | 2,538 | 13,095,625-13,098,163 | No/S | TARP | |
| | | | | | 11p15.1 | Loss | 12,459 | 18,905,796-18,918,255 | No/NS | MRGPRX1 | |
| | | | | | 14q11.2 | Loss | 219,458 | 19,272,965-19,492,423 | No/S | 6 genes | |

TABLE 1-continued

| Sample ID | Phenotype/Family type | Cytogenetic Analysis | | | CNV Analysis | | | | | |
|---|---|---|---|---|---|---|---|---|---|---|
| | | Karyotype | Breakpoint Location | RefSeq Genes | Chr | CNV | Size (bp) | Location | AS/Str[a] | RefSeq Genes | Comments |
| | | | | | 14q32.33 | Gain | 27,408 | 106,223,861-106,251,269 | No/NS | No known genes | |
| | | | | | 15q11.2-q13.3 | Gain | 11,871,747 | 18,427,100-30,296,847 | Yes/S | >50 genes | |
| | | | | | 19p13.2 | Loss | 132,251 | 6,902,567-7,034,818 | No/S | EMR4, FLG25758, MBD3L2, ZF557 | NFLD |
| 30 NA0097-000 (82361L) | Simplex Family ASD | 46, XX, t(11:12)(q23.3:p13.3) unknown | 11q23: not available | | 2p25.3-2p15 | Gain | 63,451,406[b] | 2,994-63,454,400 | Yes/S | >50 genes | |
| | | | | | 3p24.2 | Loss | 159,273 | 25,980,400-26,139,673 | No/NS | No known genes | |
| | | | | | 12p11.21 | Gain | 236,006 | 31,065,545-31,301,551 | No/S | DDX11, OVOS2 | |
| | | | | | 14q11.2 | Gain | 489,269 | 21,498,204-21,987,473 | No/NS | No known genes | |
| 31 SK0300-003 (77447) | Multiplex Family ASD, NF1 | 46, X, inv(Y)(p11.2q11.2)pat inherited | 12p13.32-p13.31: 4,341,718-7,918,138 Not available | Multiple genes | Xp22.33-Xp22.31 | Loss | 5,825,311 | 34,419-5,859,730 | Yes/S | 21 genes | |
| | | | | | 4p16.1 | Gain | 35,832 | 7,801,488-7,837,320 | Yes/NS | SORCS2 | SK |
| | | | | | 5p15.33 | Gain | 124,530 | 752,190-876,820 | No/S | ZDHHC11 | |
| | | | | | 6p25.1 | Loss | 215,567 | 4,200,904-4,416,471 | Yes/S | No known genes | |
| | | | | | 8q24.23 | Loss | 198,193 | 137,757,137-137,955,330 | No/S | No known genes | |
| | | | | | 11q15.4 | Loss | 54,390 | 6,845,440-6,899,830 | Yes/S | OR10A2, OR10A4, OR2D2, OR2D3 | |
| | | | | | 14q11.2 | Loss | 229,676 | 19,272,965-19,502,641 | No/NS | 6 genes | |
| | | | | | 15q11.2 | Loss | 1,908,355 | 18,427,103-20,335,459Error! Hyperlink reference not valid. | No/S | LOC283755, POTE15, OR4M2, OR4N4 | |
| | | | | | 15q21.2 | Gain | 183,903 | 48,583,127-46,767,030 | Yes/S | TRPM7, USP50 | |
| | | | | | Xp11.23 | Loss | 83,750 | 47,643,250-47,727,400 | No/S | ZNF630, SSX6 | |
| 32 SK0094-005 (49304) | Multiplex Family ASD | 46, XX, ins(21:?)(p11.2:?) unknown | Not available | | 7q21.2 | Loss | 509,800 | 90,919,200-91,429,000 | Yes/NS | MTERF, AKAP9, CYP51A1, LOC401387 | SK |
| | | | | | 9q32 | Gain | 211,000 | 112,463,000-112,674,900 | No/NS | KIAA1958, C9orf80 | |
| | | | | | 10q11.22 | Gain | 124,800 | 47,030,100-47,154,900 | No/NS | No known genes | |

TABLE 1-continued

| Sample ID | Phenotype/Family type | Cytogenetic Analysis | | | CNV Analysis | | | | | |
|---|---|---|---|---|---|---|---|---|---|---|
| | | Karyotype | Breakpoint Location | RefSeq Genes | Chr | CNV | Size (bp) | Location | AS/Str[a] | RefSeq Genes | Comments |
| | | | | | 14q32.33 | Gain | 186,000 | 105,829,000-106,015,000 | No/NS | No known genes | |
| | | | | | Xq23 | Loss | 888,000 | 112,325,000-113,213,000 | Yes/NS | No known genes | |

Affymetrix GeneChip Human Mapping 500K Array Set

For each sample, approximately 500,000 SNPs were genotyped using the combined two-chip Nspl and Styl GeneChip® Human Mapping Commercial or Early Access Arrays (Affymetrix, Inc., Santa Clara, Calif.) according to the manufacturer's instructions and as described previously (Kennedy et al. 2003 Nat Biotechnol. 21:1233-7, the contents of which are incorporated herein by reference). Briefly, 250 ng of genomic DNA was digested with Nspl and Styl restriction enzyme (New England Biolabs, Boston, Mass.), ligated to an adaptor and amplified by PCR. The PCR products were then fragmented with DNaseI to a size range of 250 bp to 2,000 bp, labelled, and hybridized to the array. After hybridization, arrays were washed on the Affymetrix fluidics stations, stained, and scanned using the Gene Chip Scanner 3000 7G and Gene Chip Operating System. Data has been submitted to the Gene Expression Omnibus database (accession GSE9222). Karyotypes were generated using standard clinical diagnostic protocols.

Characterization of Copy Number Variation

Nspl and Styl array scans were analyzed for copy number variation using a combination of DNA Chip Analyzer (dChip) (Li and Wong 2001 *Genome Biology* 2: 0032.1-0032.11), Copy Number Analysis for GeneChip (CNAG) (Nannya 2005 *Cancer Res.* 65:6071-9) and Genotyping Microarray based CNV Analysis (GEMCA) (Komura 2006 *Genome Res.* 16:1575-84). Each of these references is incorporated herein by reference.

Analysis with dChip (www.dchip.org) was performed as previously described (Zhao et al 2005 *Cancer Res.* 65:5561-70) in batches of ~100 probands. Briefly, array scans were normalized at the probe intensity level with an invariant set normalization method. After normalization, a signal value was calculated for each SNP using a model-based (PM/MM) method. In this approach, image artifacts were identified and eliminated by an outlier detection algorithm. For both sets of arrays, the resulting signal values were averaged across all samples for each SNP to obtain the mean signal of a diploid genome. From the raw copy numbers, the inferred copy number at each SNP was estimated using a Hidden Markov Model (HMM).

For analyses with CNAG version 2.0 (www.genome.umin.jp), the reference pool was set to include all samples and performed an automatic batch pair-wise analysis using sex-matched controls. Test samples were compared to all samples within the reference pool and matched based on signal intensity standard deviations. The scan intensities for each 'test' sample were compared to the average intensities of the reference samples (typically the average of 5-12 samples) and used to calculate raw copy number changes. Underlying copy number changes were then inferred using a Hidden Markov Model (HMM) built into CNAG.

GEMCA analysis was performed essentially as described (Komura et al. Genome Res 2006; 16(12):1575-84) with the exception that two designated DNA samples (NA10851 and NA15510) were used as references for pair-wise comparison to all proband experiments. These results were further filtered by only including those CNVs that were common to both pair-wise experiments.

CNVs were merged if they were detected in the same individual by more than one algorithm using the outside probe boundaries.

Controls and Autism Chromosome Rearrangement Database (ACRD)

Control samples consisted of (i) CNVs observed in 500 Europeans from the from the German PopGen project (Krawczak et al. Community Genet 2006; 9(1):55-61), and CNVs found in a cohort of 1000 Caucasian non-disease controls from the Ontario population (ref. 24). The ACRD that had 834 putative CNVs or breakpoints mapped to the genome was established. A CNV was considered ASD-specific if it was >10 kb, contained at least three probes and at least 20% of its total length was unique when compared to controls.

CNV Validation Experiments and Balance Rearrangement Breakpoint Mapping

PCR validation of CNV calls was performed using Quantitative Multiplex PCR of short fluorescent fragments (QMPSF) (Redon et al. Nature. 444:444-54) or SYBR-Green 1 based real-time quantitative PCR (qPCR) using controls at the ACCN1, CFTR or FOXP2 loci (PMID: 14552656). For both methods, primers were designed using the program PRIMER3 (http://frodo.wi.mit.edu/). Balanced rearrangements were mapped primarily using FISH (Nannya et al. Cancer Res 2005; 65(14):6071-9). The microdel program (Komura et al., ibid) was used to score CNV losses.

For QMPSF, short genomic sequences (140-220 bp) within putative CNVs were PCR amplified using dye-labelled primers corresponding to unique sequences. Each reaction also included co-amplified control amplicons corresponding to either ACCN1 or CFTR located at 17q11.2 and 7q31.2, respectively. Briefly, 40 ng of genomic DNA was amplified by PCR in a final volume of 25 µl using AmpliTaq® DNA polymerase (manufactured for Applied Biosystems by Roche Molecular Systems, Inc.) After an initial step of denaturation at 95° C. for 5 minutes conditions were as follows: 25 PCR cycles of 94° C. for 30 seconds, annealing at 60° C. for 45 seconds, and extension at 72° C. for 30 seconds. A final extension step at 72° C. for 15 minutes followed. QMPSF amplicons were separated on an ABI 3730 xl DNA Analyzer (Applied Biosystems, Foster City, Calif.), and analyzed using ABI GeneMapper® software version 3.7 (Applied Biosystems). After adjustment of control amplicons to the same heights, the QMPSF pattern generated from test DNA was superimposed to that of the control DNA. For each putative CNV locus, the copy number ratio was determined by dividing the normalized peak height obtained from the test DNA by that of the control DNA. Peak ratios of >1.4 and <0.7 were indicative of copy number gains and losses, respectively. At least two independent QMPSF assays were required for CNV confirmation.

SYBR Green I-based real-time qPCR amplification was performed using a Mx3005P quantitative PCR system (Stratagene, La Jolla, USA). Non-fluorescent primers were designed to amplify short genomic fragments (<140 bp) in putative CNV loci. Each assay also included amplification of a control amplicon corresponding to FOXP2 at 7q31.1 for comparison. After optimization of primer sets with control genomic DNA using 'Brilliant® SYBR® Green QPCR Master Mix' (Stratagene), test samples were assayed in 15 µl reaction mixtures in 96-well plates containing: 7.5 µl of reaction mix, 1.8 µl of primer, 6.0 ng of genomic DNA at 1.2 ng/µl, 0.225 µl of reference dye with 1:500 dilution, and 0.475 µl of water. PCR conditions consisted of 10 minutes of polymerase activation at 95° C., followed by 40 cycles of: 95° C. for 15 seconds and a single step at 60° C. for 1 minute for annealing and elongation. These steps were then followed by a final cycle of 95° C. for 1 minute, 55° C. for 30 seconds, and 95° C. for 30 seconds. Standard curve quantification was analyzed by MxPro-Mx3005P software (version 3.20 Build 340) to calculate copy number changes. Coefficient of variation (CV) was calculated on all sample Ct values to remove possible outlier when CV was greater than 1%. The average quantity of the putative CNV locus was divided by the average quantity of the control amplicon on FOXP2. Ratios of >1.4 and <0.7 were indicative of copy number gains and losses, respectively. Each putative CNV locus had at least two independent assays.

Results

Structural Variation Characteristics in ASD Cases

A total of 426 ASD index cases were tested for CNV content including 394 typical idiopathic cases and 32 others that were enrolled based on prior knowledge of having a cytogenetic abnormality. The Affymetrix 500k SNP array was used because it provided the highest resolution screen available for both SNP genotype and CNV data. Using the SNPs, the ancestry of each sample was categorized (to guide selection of controls). Backgrounds of the samples were found to be: 90.3%, 4.5%, 4.5%, and 0.7%, European, European/mixed, Asian, or Yoruban, respectively.

To maximize CNV discovery, three calling algorithms were used as described above (see FIG. 1) and common results between them were merged to identify a 'full' dataset of 3389 independent CNVs (~8 CNVs per genome, mean size 390 kb) (see Table 4 below). To minimize potential false positives, a second dataset was generated whereby a CNV needed to be detected by two or more algorithms and/or on both the NspI or StyI microarrays (Pinto et al. Hum Mol Genet 2007; 16 Spec No 2:R168-73).

This 'stringent' dataset contained 1312 CNVs (~3 CNVs per genome, mean size 603 kb). Using q-PCR, 48% (12/26) and 96% (48/50) of random CNVs were validated in the full and stringent collections, respectively.

TABLE 4

Summary of CNV in ASD and Controls

| | POPGEN CONTROLS | | AUTISM PROBANDS | | | |
| --- | --- | --- | --- | --- | --- | --- |
| | All CNVs | | All CNVs | | Autism Specific[1] | |
| | Full | Stringent[2] | Full | Stringent[2] | Full | Stringent[2] |
| #samples | 500 | 500 | 426 | 426 | 426 | 426 |
| #CNVs | 3695 | 1558 | 3389 | 1312 | 888 | 276 |
| CNV/Genome[3] | 7.4 | 3.1 | 8.0 | 3.1 | 2.1 | 0.65 |
| Mean/Median Size (kb) | 315/151 | 470/224 | 390/162 | 603/219 | 518/121 | 1082/194 |
| % Gain/Loss | 59/41% | 70/30% | 58/42% | 62/38% | 61/39% | 57/43% |
| Overlapping CNV/Loci (%)[4] | 3005/333 (81%) | 1226/142 (78%) | 2728/277 (80%) | 980/94 (74%) | 397/122 (44%) | 30/13 (11%) |
| >1 Mb CNV(%) | 343(9%) | 250(16%) | 339(10%) | 212(16%) | 63(7%) | 32(12%) |

[1]Not seen in controls.
[2]Stringent dataset as called by >1 algorithms or arrays. Analysis with dChip was performed in batches of ~100 probands. For CNAG version 2.0, the reference pool was set to include all samples and performed an automatic batch pairwise analysis using sex-matched controls. For GEMCA two designated DNA samples (NA10851 and NA15510) were used as references for pairwise comparison to all proband experiments. These results were further filtered by only including those CNVs that were common to both pairwise experiments. In all instances CNVs were merged if they were detected in the same individual by more than one algorithm using the outside probe boundaries.
[3]CNV/genome breakdown by algorithm: dChip Merged (3.0/genome), CNAG Merged (5.6/genome), GEMCA (5.5/genome). Validation experiments using q-PCR and FISH are described in the text. Another form of validation comes from examining the trios where we can demonstrate inheritance in 48 (maternal is 25, paternal is 23) of the autism-specific stringent dataset. Also from the trios, 148 confirmed regions (inheritance assignment) in the stringent dataset that overlap with controls (maternal is 65, paternal is 83).
[4]Represents the total number of overlapping and/or recurrent CNVs, the number of overlapping/CNV loci, and the percentage of overlapping CNVs, out of the total dataset.

Five hundred European control samples were examined for their CNV content and similar numbers of CNVs (3695 in the full and 1558 in the stringent dataset) were found to those in the ASD cases (Table 4). This suggested germ-line chromosome instability was not a significant contributing mechanism. The ASD CNVs were then compared against the 500 European/Caucasian controls and the *Database of Genomic Variants* (a repository of structural variation in 'non-disease' populations) (Iafrate et al. Nat Genet 2004; 36(9):949-51) to establish autism-specific CNV datasets. The subsequent analysis then focused on the 276 CNVs in the stringent autism-specific category, which mapped across all 23 chromosomes (FIG. 2), details of which are found in Table 3, below. Additional ASD-relevant CNV data is also found in the other categories in Table 5 (discussed below).

TABLE 3

| FAM ID (DNA) | Sex | Type | Chr | start | stop | size | CNV | CNV Category |
| --- | --- | --- | --- | --- | --- | --- | --- | --- |
| SK0215-006 (58449) | M | CHR | 1 | 97,271,600 | 98,364,100 | 1,092,500 | loss | CNVs confirmed de novo |
| SK0152-003 (41548L) | M | CHR | 3 | 15,125,800 | 16,535,400 | 1,409,600 | loss | CNVs confirmed de novo |
| SK0181-003 (52191) | M | CHR | 3 | 65,286,300 | 70,633,200 | 5,346,900 | loss | CNVs confirmed de novo |
| SK0205-004 (56242) | r | CHR | 5 | 81,949 | 13,882,933 | 13,800,984 | loss | CNVs confirmed de novo |
| SK0152-003 (41548L) | M | CHR | 5 | 9,275,811 | 12,705,200 | 3,429,389 | loss | CNVs confirmed de novo |
| SK0083-003 (50800L) | M | CHR | 7 | 108,200,381 | 119,223,887 | 11,023,507 | loss | CNVs confirmed de novo |
| SK0131-003 (39989) | F | CHR | 7 | 113,335,000 | 128,821,721 | 15,486,722 | loss | CNVs confirmed de novo |
| SK0262-003 (68609) | M | SPX | 8 | 710,491 | 1,501,580 | 791,089 | gain | CNVs confirmed de novo |

TABLE 3-continued

| FAM ID (DNA) | Sex | Type | Chr | start | stop | size | CNV | CNV Category |
|---|---|---|---|---|---|---|---|---|
| SK0152-003 (41548L) | M | CHR | 12 | 40,584,198 | 41,007,040 | 422,842 | loss | CNVs confirmed de novo |
| MM0278-003 (57788) | M | SPX | 12 | 114,170,000 | 132,388,001 | 18,218,001 | loss | CNVs confirmed de novo |
| SK0243-003 (67941) | M | CHR | 15 | 69,601,300 | 73,890,800 | 4,289,500 | loss | CNVs confirmed de novo |
| NA0067-000 (65344L) | M | SPX | 16 | 87,800,593 | 88,066,260 | 265,668 | loss | CNVs confirmed de novo |
| SK0218-003 (60340) | F | CHR | 18 | 55,756,601 | 76,115,600 | 20,358,999 | loss | CNVs confirmed de novo |
| MM0109-003 (46486) | F | SPX | 20 | 60,949,339 | 62,377,000 | 1,427,662 | gain | CNVs confirmed de novo |
| SK0244-003 (69183) | M | SPX | 21 | 42,974,148 | 43,328,084 | 353,936 | gain | CNVs confirmed de novo |
| NA0039-000 (69736) | F | CHR | 22 | 46,277,400 | 49,509,100 | 3,231,700 | loss | CNVs confirmed de novo |
| MM0109-003 (46486) | F | SPX | 22 | 49,243,247 | 49,519,949 | 276,703 | loss | CNVs confirmed de novo |
| NA0097-000 (82361L) | F | CHR | X | 34,419 | 5,859,730 | 5,825,312 | loss | CNVs confirmed de novo |
| SK0306-004 (78681) | F | SPX | X | 48,073,600 | 52,716,966 | 4,643,367 | gain | CNVs confirmed de novo |
| SK0147-003 (47544L) | F | SPX | 2 | 114,855,796 | 115,334,166 | 478,371 | loss | CNVs Recurrent/Overlap |
| SK0167-003 (60966L) | F | MPX | 2 | 114,855,796 | 115,334,166 | 478,371 | gain | CNVs Recurrent/Overlap |
| SK0288-003 (75420) | F | SPX-MZ | 2 | 115,141,880 | 115,247,000 | 105,121 | gain | CNVs Recurrent/Overlap |
| NA0030-000 (55240) | F | SPX | 2 | 186,674,000 | 186,786,323 | 112,324 | loss | CNVs Recurrent/Overlap |
| SK0306-004 (78681) | F | SPX | 2 | 186,674,000 | 186,771,130 | 97,131 | loss | CNVs Recurrent/Overlap |
| MM0220-003 (61180L) | M | MPX | 6 | 118,799,000 | 119,117,000 | 318,001 | gain | CNVs Recurrent/Overlap |
| NA0025-000 (60490) | M | SPX | 6 | 118,823,011 | 119,117,000 | 293,990 | gain | CNVs Recurrent/Overlap |
| SK0190-003 (54742) | M | SPX | 7 | 152,698,000 | 154,478,000 | 1,780,000 | gain | CNVs Recurrent/Overlap |
| SK0115-003 (40555) | M | SPX | 7 | 153,098,000 | 153,372,000 | 274,001 | gain | CNVs Recurrent/Overlap |
| SK0058-003 (59963) | M | MPX | 7 | 153,539,745 | 153,556,533 | 16,789 | gain | CNVs Recurrent/Overlap |
| SK0143-003 (36812) | M | SPX | 8 | 53,481,200 | 53,766,400 | 285,201 | gain | CNVs Recurrent/Overlap |
| MM0236-004 (46475) | M | MPX | 8 | 53,724,445 | 53,996,124 | 271,680 | gain | CNVs Recurrent/Overlap |
| SK0270-003 (71341) | M | SPX | 9 | 7,725,280 | 7,764,180 | 38,900 | loss | CNVs Recurrent/Overlap |
| MM0103-003 (42387) | M | MPX | 9 | 7,725,283 | 7,760,233 | 34,951 | loss | CNVs Recurrent/Overlap |
| MM0272-003 (45563) | M | MPX | 11 | 40,285,800 | 40,548,738 | 262,939 | loss | CNVs Recurrent/Overlap |
| SK0167-003 (60966L) | F | MPX | 11 | 40,417,554 | 40,610,401 | 192,847 | loss | CNVs Recurrent/Overlap |
| SK0023-003 (58096) | M | SPX | 13 | 66,470,851 | 66,660,289 | 189,438 | gain | CNVs Recurrent/Overlap |
| MM0299-003 (51674) | F | MPX | 13 | 66,487,899 | 66,660,300 | 172,402 | gain | CNVs Recurrent/Overlap |
| MM0109-003 (46486) | F | SPX | 16 | 21,441,805 | 22,688,093 | 1,246,289 | gain | CNVs Recurrent/Overlap |
| MM0289-003 (42267) | F | MPX | 16 | 21,808,808 | 22,611,363 | 802,556 | loss | CNVs Recurrent/Overlap |
| MM0088-003 (45562) | F | MPX | 16 | 29,559,989 | 30,235,818 | 675,830 | gain | CNVs Recurrent/Overlap |
| NA0133-000 (78119L) | F | SPX | 16 | 29,559,989 | 30,085,308 | 525,320 | gain | CNVs Recurrent/Overlap |
| SK0091-004 (46407) | F | MPX | 22 | 17,265,500 | 21,546,762 | 4,281,262 | gain | CNVs Recurrent/Overlap |
| SK0323-003 (80022) | M | MPX | 22 | 18,683,900 | 19,427,000 | 743,101 | gain | CNVs Recurrent/Overlap |
| SK0123-004 (60536L) | M | MPX | 22 | 47,717,300 | 48,318,828 | 601,528 | gain | CNVs Recurrent/Overlap |
| MM0102-003 (47598) | M | MPX | 22 | 48,152,289 | 48,232,669 | 80,380 | loss | CNVs Recurrent/Overlap |
| NA0002-000 (52026) | M | SPX | 7 | 153,585,000 | 153,651,462 | 66,463 | loss | CNVs Recurrent/Overlap CNVs confirmed de novo |
| SK0073-003 (57283L) | F | CHR | 15 | 18,376,200 | 30,298,800 | 11,922,600 | gain | CNVs confirmed de novo CNVs Recurrent/Overlap |
| SK0245-005 (68517) | M | CHR | 15 | 18,427,100 | 30,298,847 | 11,871,747 | gain | CNVs Recurrent/Overlap CNVs confirmed de novo |
| SK0119-003 (35190) | M | MPX | 22 | 17,014,900 | 19,786,200 | 2,771,300 | loss | CNVs Recurrent/Overlap |
| SK0297-003 (76066) | M | SPX-MZ | 22 | 17,265,500 | 21,546,762 | 4,281,263 | gain | CNVs Recurrent/Overlap CNVs confirmed de novo |
| MM0109-003 (46486) | F | SPX | 17 | 40,555,289 | 41,089,766 | 534,478 | loss | CNVs that are Singletons |
| MM0240-003 (43743) | F | MPX | 17 | 40,555,289 | 41,128,323 | 573,035 | loss | CNVs that are Singletons |
| NA0074-000 (63358) | M | SPX | 1 | 41,463,611 | 41,924,314 | 960,704 | gain | CNVs that are Singletons |
| SK0036-003 (29186) | F | SPX | 1 | 57,936,233 | 58,514,629 | 578,396 | gain | CNVs that are Singletons |
| MM0236-004 (46475) | M | MPX | 1 | 60,369,200 | 61,426,300 | 1,057,101 | gain | CNVs that are Singletons |
| MM0020-004 (47838) | M | MPX | 1 | 65,649,086 | 65,713,424 | 64,338 | gain | CNVs that are Singletons |
| NA0076-000 (63624) | M | SPX | 1 | 91,930,266 | 92,330,344 | 400,078 | gain | CNVs that are Singletons |
| SK0174-003 (64379L) | M | SPX | 1 | 108,046,000 | 108,246,283 | 200,284 | loss | CNVs that are Singletons |
| SK0283-003 (72309) | F | CHR | 1 | 148,095,537 | 149,547,463 | 1,451,926 | gain | CNVs that are Singletons |
| MM0011-003 (60566L) | M | MPX | 1 | 165,908,677 | 166,028,402 | 119,726 | loss | CNVs that are Singletons |
| SK0132-003 (30661) | M | MPX | 1 | 186,673,899 | 186,716,570 | 42,672 | loss | CNVs that are Singletons |
| NA0109-000 (72873) | M | SPX | 1 | 212,037,558 | 212,971,000 | 433,443 | loss | CNVs that are Singletons |
| SK0183-004 (52217) | M | SPX | 1 | 238,633,145 | 239,606,926 | 973,781 | loss | CNVs that are Singletons |
| MM0219-003 (46823) | M | MPX | 2 | 34,155,700 | 34,253,221 | 97,522 | loss | CNVs that are Singletons |
| MM0295-003 (46488) | M | MPX | 2 | 34,662,196 | 34,780,515 | 118,320 | loss | CNVs that are Singletons |
| NA0083-000 (66104L) | M | SPX | 2 | 34,858,330 | 34,937,455 | 79,125 | loss | CNVs that are Singletons |
| SK0270-003 (71341) | M | SPX | 2 | 39,992,374 | 40,053,300 | 60,926 | loss | CNVs that are Singletons |
| NA0055-000 (59448) | M | SPX | 2 | 41,958,200 | 42,088,448 | 130,249 | loss | CNVs that are Singletons |
| SK0301-003 (77203) | M | MPX | 2 | 52,856,046 | 52,969,575 | 113,530 | loss | CNVs that are Singletons |
| NA0027-000 (60421L) | M | MPX | 2 | 121,623,000 | 121,684,915 | 61,915 | loss | CNVs that are Singletons |
| NA0057-000 (59537) | M | SPX | 2 | 125,496,832 | 125,890,571 | 393,740 | loss | CNVs that are Singletons |
| MM0176-003 (62118L) | M | MPX | 2 | 135,358,000 | 135,471,070 | 113,071 | loss | CNVs that are Singletons |
| SK0225-003 (60921) | M | SPX | 2 | 155,849,451 | 155,988,560 | 139,109 | loss | CNVs that are Singletons |
| SK0192-003 (54877) | M | SPX | 2 | 181,771,621 | 181,944,065 | 172,445 | loss | CNVs that are Singletons |
| NA0007-000 (50611) | M | SPX | 2 | 195,170,000 | 195,217,247 | 47,248 | gain | CNVs that are Singletons |
| SK0283-003 (72309) | F | CHR | 3 | 5,366,506 | 5,409,964 | 44,458 | loss | CNVs that are Singletons |
| MM0210-004 (47376) | M | MPX | 3 | 7,957,390 | 8,250,541 | 293,151 | gain | CNVs that are Singletons |
| NA0044-000 (57097) | M | SPX | 3 | 35,613,300 | 35,928,200 | 314,901 | gain | CNVs that are Singletons |
| SK0021-008 (51504) | M | MPX | 3 | 36,110,965 | 36,215,909 | 104,945 | loss | CNVs that are Singletons |
| MM0154-003 (56678L) | P | MPX | 3 | 50,089,500 | 50,199,200 | 109,701 | gain | CNVs that are Singletons |
| SK0152-003 (41548L) | M | CHR | 3 | 78,902,000 | 78,957,000 | 55,000 | gain | CNVs that are Singletons |
| NA0044-000 (57097) | M | SPX | 3 | 82,866,400 | 84,544,763 | 1,678,364 | gain | CNVs that are Singletons |

TABLE 3-continued

| FAM ID (DNA) | Sex | Type | Chr | start | stop | size | CNV | CNV Category |
|---|---|---|---|---|---|---|---|---|
| SK0023-003 (58096) | M | SPX | 3 | 99,400,957 | 99,484,400 | 83,943 | gain | CNVs that are Singletons |
| NA0018-000 (72622) | M | SPX | 3 | 117,838,700 | 117,937,000 | 98,301 | gain | CNVs that are Singletons |
| NA0003-000 (48474) | M | SPX | 3 | 124,386,373 | 124,456,000 | 69,628 | gain | CNVs that are Singletons |
| NA0090-000 (65410) | M | SPX | 3 | 183,837,706 | 183,940,069 | 102,364 | gain | CNVs that are Singletons |
| NA0044-000 (57097) | M | SPX | 4 | 55,718,164 | 55,811,710 | 93,547 | loss | CNVs that are Singletons |
| NA0016-000 (51524L) | F | SPX | 4 | 114,333,509 | 114,416,051 | 82,542 | gain | CNVs that are Singletons |
| SK0012-003 (58468L) | M | SPX | 4 | 152,993,000 | 153,381,007 | 388,008 | gain | CNVs that are Singletons |
| SK0103-005 (42258) | M | SPX | 9 | 157,615,000 | 157,683,000 | 68,000 | gain | CNVs that are Singletons |
| NA0037-000 (69812) | M | SPX | 4 | 179,692,000 | 179,865,679 | 173,680 | gain | CNVs that are Singletons |
| MM0299-003 (51674) | F | MPX | 9 | 181,968,784 | 182,095,665 | 126,882 | loss | CNVs that are Singletons |
| SK0266-003 (68257) | M | SPX | 4 | 183,466,000 | 183,517,000 | 51,000 | loss | CNVs that are Singletons |
| SK0002-003 (50002) | F | CHR | 5 | 14,940,400 | 15,179,500 | 239,100 | gain | CNVs that are Singletons |
| NA0078-000 (63727) | M | MPX | 5 | 25,125,371 | 25,450,672 | 325,302 | gain | CNVs that are Singletons |
| NA0076-000 (63624) | M | SPX | 5 | 37,409,881 | 37,778,834 | 368,953 | gain | CNVs that are Singletons |
| SK0335-003 (72815) | F | CHR | 5 | 38,534,384 | 38,807,002 | 272,619 | loss | CNVs that are Singletons |
| MM0143-004 (47386) | M | MPX | 5 | 110,440,984 | 110,471,180 | 30,697 | gain | CNVs that are Singletons |
| NA0023-000 (60504L) | F | SPX | 5 | 113,104,916 | 113,178,000 | 73,084 | loss | CNVs that are Singletons |
| SK0118-003 (52027) | M | SPX | 5 | 122,834,399 | 123,029,036 | 194,638 | loss | CNVs that are Singletons |
| SK0077-003 (48226) | M | SPX | 5 | 128,968,799 | 129,433,000 | 464,201 | gain | CNVs that are Singletons |
| SK0300-003 (77447) | M | CHR | 6 | 4,200,904 | 4,416,471 | 215,568 | loss | CNVs that are Singletons |
| MM0212-004 (62223L) | F | MPX | 6 | 17,505,095 | 17,703,208 | 198,114 | gain | CNVs that are Singletons |
| MM0300-003 (47836) | F | MPX | 6 | 27,827,354 | 28,119,631 | 292,278 | gain | CNVs that are Singletons |
| MM0225-004 (60826) | M | MPX | 6 | 69,929,900 | 70,278,043 | 348,144 | gain | CNVs that are Singletons |
| SK0217-003 (59279) | M | SPX | 6 | 112,679,982 | 112,776,094 | 96,112 | gain | CNVs that are Singletons |
| SK0326-003 (81155) | M | SPX | 5 | 137,930,847 | 138,011,644 | 80,798 | gain | CNVs that are Singletons |
| MM0088-003 (45562) | F | MPX | 7 | 2,922,139 | 2,964,895 | 42,757 | loss | CNVs that are Singletons |
| NA0147-000 (77123L) | M | SPX | 7 | 3,946,854 | 4,002,686 | 55,833 | gain | CNVs that are Singletons |
| SK0049-004 (59987L) | M | MPX | 7 | 11,526,500 | 11,560,300 | 33,800 | gain | CNVs that are Singletons |
| SK0132-003 (30661) | M | MPX | 7 | 20,242,925 | 20,345,800 | 102,876 | gain | CNVs that are Singletons |
| NA0145-000 (82058L) | M | SPX | 7 | 47,742,927 | 48,775,200 | 1,032,274 | loss | CNVs that are Singletons |
| SK0119-003 (35190) | M | MPX | 8 | 17,706,313 | 17,738,524 | 32,211 | loss | CNVs that are Singletons |
| SK0262-003 (68609) | M | SPX | 8 | 18,623,000 | 19,442,500 | 819,500 | gain | CNVs that are Singletons |
| SK0077-003 (48226) | M | SPX | 8 | 42,971,601 | 43,820,300 | 848,699 | gain | CNVs that are Singletons |
| SK0294-003 (76222) | M | SPX | 8 | 73,762,894 | 73,798,241 | 35,348 | gain | CNVs that are Singletons |
| SK0076-003 (38712) | F | SPX | 8 | 83,989,256 | 84,141,278 | 152,022 | gain | CNVs that are Singletons |
| MM0241-004 (45547) | M | MPX | 8 | 87,230,811 | 87,498,988 | 268,178 | gain | CNVs that are Singletons |
| MM0210-004 (47376) | M | MPX | 8 | 104,166,572 | 104,947,190 | 780,618 | gain | CNVs that are Singletons |
| SK0194-003 (55078) | M | SPX | 8 | 123,539,127 | 123,644,422 | 105,296 | loss | CNVs that are Singletons |
| SK0292-003 (75896) | F | MPX | 8 | 130,467,000 | 130,529,193 | 62,194 | loss | CNVs that are Singletons |
| MM0007-003 (59978) | M | MPX | 9 | 5,099,530 | 5,235,490 | 135,961 | gain | CNVs that are Singletons |
| MM0711-003 (63583L) | M | MPX | 9 | 16,092,066 | 16,379,100 | 287,035 | gain | CNVs that are Singletons |
| SK0015-003 (49932) | M | MPX | 9 | 19,284,100 | 19,511,500 | 227,400 | gain | CNVs that are Singletons |
| SK0015-003 (49932) | M | SPX | 9 | 19,702,200 | 24,674,100 | 4,971,900 | loss | CNVs that are Singletons |
| SK0278-003 (74431) | M | SPX | 9 | 22,526,541 | 22,747,715 | 121,174 | loss | CNVs that are Singletons |
| SK0148-005 (41350) | F | SPX | 9 | 24,607,036 | 24,682,114 | 75,078 | loss | CNVs that are Singletons |
| MM0020-004 (47838) | M | MPX | 9 | 25,439,100 | 25,535,000 | 95,901 | loss | CNVs that are Singletons |
| NA0105-000 (72085) | M | SPX | 9 | 33,054,336 | 33,294,800 | 240,465 | gain | CNVs that are Singletons |
| NA0147-000 (77123L) | M | SPX | 9 | 84,957,060 | 85,054,673 | 97,613 | loss | CNVs that are Singletons |
| SK0045-003 (58937) | M | MPX | 9 | 109,446,000 | 109,837,000 | 391,000 | gain | CNVs that are Singletons |
| MM0117-003 (59983) | M | MPX | 10 | 2,313,505 | 2,407,102 | 93,598 | loss | CNVs that are Singletons |
| MM0225-004 (60826) | M | MPX | 10 | 4,976,040 | 5,124,511 | 148,472 | gain | CNVs that are Singletons |
| MM1086-003 (76285) | M | MPX | 10 | 31,256,118 | 31,604,510 | 348,392 | gain | CNVs that are Singletons |
| MM0068-003 (60836) | M | MPX | 10 | 68,139,200 | 68,246,027 | 106,828 | gain | CNVs that are Singletons |
| NA0037-000 (69812) | M | SPX | 10 | 104,641,000 | 104,786,777 | 145,778 | loss | CNVs that are Singletons |
| SK0300-003 (77447) | M | CHR | 11 | 6,845,440 | 6,899,830 | 54,391 | loss | CNVs that are Singletons |
| SK0322-003 (79950) | M | SPX | 11 | 33,159,190 | 33,462,070 | 302,881 | gain | CNVs that are Singletons |
| MM0305-003 (47607) | M | MPX | 11 | 68,053,777 | 68,204,900 | 151,123 | gain | CNVs that are Singletons |
| NA0032-000 (55486) | M | SPX | 11 | 76,114,600 | 76,140,500 | 25,900 | gain | CNVs that are Singletons |
| MM0212-004 (62223L) | F | MPX | 11 | 99,148,202 | 99,289,243 | 141,042 | loss | CNVs that are Singletons |
| SK0167-003 (60966L) | F | MPX | 11 | 101,131,785 | 101,246,901 | 115,117 | loss | CNVs that are Singletons |
| MM0112-005 (46738) | M | MPX | 11 | 116,789,980 | 116,856,347 | 66,368 | gain | CNVs that are Singletons |
| MM0240-003 (43743) | F | MPX | 11 | 117,452,000 | 117,539,000 | 87,001 | gain | CNVs that are Singletons |
| SK0255-003 (68785) | M | SPX | 11 | 124,303,460 | 124,719,976 | 416,517 | gain | CNVs that are Singletons |
| NA0065-000 (62798L) | M | SPX | 11 | 125,639,908 | 126,102,027 | 462,120 | gain | CNVs that are Singletons |
| NA0172-000 (80993L) | M | SPX | 12 | 3,727,911 | 3,879,230 | 151,320 | gain | CNVs that are Singletons |
| SK0059-003 (29224) | M | SPX | 12 | 10,431,082 | 10,445,300 | 14,218 | gain | CNVs that are Singletons |
| SK0326-003 (81155) | M | SPX | 12 | 46,170,200 | 46,365,774 | 196,675 | gain | CNVs that are Singletons |
| SK0110-003 (24626) | M | SPX | 12 | 50,520,400 | 50,573,516 | 53,416 | gain | CNVs that are Singletons |
| NA0071-000 (64719L) | F | SPX | 12 | 57,408,270 | 58,532,356 | 1,124,087 | gain | CNVs that are Singletons |
| SK0305-003 (78621) | F | SPX | 12 | 77,239,265 | 77,364,400 | 125,136 | loss | CNVs that are Singletons |
| SK0301-003 (77203) | M | MPX | 12 | 83,388,935 | 83,428,800 | 39,866 | gain | CNVs that are Singletons |
| NA0093-000 (66999) | M | SPX | 12 | 96,496,784 | 96,568,500 | 71,716 | loss | CNVs that are Singletons |
| MM0711-003 (63583L) | M | MPX | 12 | 96,576,486 | 96,639,686 | 63,201 | loss | CNVs that are Singletons |
| SK0292-003 (75896) | F | MPX | 12 | 101,568,000 | 101,586,000 | 18,001 | gain | CNVs that are Singletons |
| NA0109-000 (72873) | M | SPX | 12 | 110,646,607 | 110,800,000 | 153,394 | loss | CNVs that are Singletons |
| MM0210-004 (47376) | M | MPX | 12 | 125,446,000 | 125,757,000 | 311,000 | gain | CNVs that are Singletons |
| SK0079-003 (48388) | M | MPX | 13 | 17,960,300 | 18,492,994 | 532,694 | gain | CNVs that are Singletons |
| NA0028-000 (58891L) | M | SPX | 13 | 62,915,912 | 62,977,748 | 61,837 | loss | CNVs that are Singletons |

TABLE 3-continued

| FAM ID (DNA) | Sex | Type | Chr | start | stop | size | CNV | CNV Category |
|---|---|---|---|---|---|---|---|---|
| SK0326-003 (81155) | M | SPX | 13 | 89,726,966 | 90,134,219 | 407,254 | gain | CNVs that are Singletons |
| NA0048-000 (58569) | M | SPX | 13 | 93,288,520 | 93,344,600 | 56,081 | gain | CNVs that are Singletons |
| SK0326-003 (81155) | M | SPX | 13 | 93,497,400 | 93,732,931 | 235,532 | gain | CNVs that are Singletons |
| SK0254-003 (68687) | M | SPX | 13 | 105,172,000 | 105,357,000 | 185,000 | gain | CNVs that are Singletons |
| SK0121-003 (41288) | M | SPX | 14 | 76,007,842 | 76,924,400 | 916,558 | gain | CNVs that are Singletons |
| SK0031-003 (68160L) | M | CHR | 14 | 99,015,100 | 99,787,500 | 772,400 | gain | CNVs that are Singletons |
| SK0300-003 (77447) | M | CHR | 15 | 48,583,127 | 48,767,030 | 183,904 | gain | CNVs that are Singletons |
| SK0326-003 (81155) | M | SPX | 15 | 97,406,000 | 97,961,522 | 555,523 | gain | CNVs that are Singletons |
| SK0281-003 (72934) | M | SPX | 16 | 57,542,779 | 57,579,900 | 37,122 | loss | CNVs that are Singletons |
| MM0310-005 (60951) | M | MPX | 16 | 80,972,252 | 80,983,135 | 10,884 | loss | CNVs that are Singletons |
| SK0203-004 (56040) | M | MPX | 16 | 82,603,600 | 82,687,900 | 84,300 | gain | CNVs that are Singletons |
| SK0085-004 (30422) | M | MPX | 17 | 3,836,592 | 3,998,867 | 162,276 | gain | CNVs that are Singletons |
| SK0298-003 (77697) | M | SPX | 17 | 76,914,079 | 77,771,141 | 857,063 | gain | CNVs that are Singletons |
| SK0328-003 (82302) | M | SPX | 18 | 13,794,043 | 14,743,900 | 949,658 | gain | CNVs that are Singletons |
| SK0303-003 (78391) | F | MPX | 18 | 28,383,551 | 28,448,100 | 64,550 | loss | CNVs that are Singletons |
| SK0014-003 (41606) | M | SPX | 18 | 52,531,252 | 53,165,421 | 634,169 | gain | CNVs that are Singletons |
| SK0121-003 (41288) | M | SPX | 19 | 33,693,363 | 33,762,805 | 69,442 | loss | CNVs that are Singletons |
| NA0111-000 (73891) | M | SPX | 19 | 57,836,600 | 58,246,200 | 409,601 | gain | CNVs that are Singletons |
| NA0004-000 (47490) | M | SPX | 19 | 58,634,965 | 58,958,584 | 323,620 | gain | CNVs that are Singletons |
| NA0070-000 (64249L) | F | SPX | 19 | 60,499,398 | 60,742,656 | 243,259 | loss | CNVs that are Singletons |
| SK0047-003 (47173L) | F | SPX | 19 | 61,910,800 | 62,644,900 | 734,100 | loss | CNVs that are Singletons |
| NA0110-000 (72165) | M | SPX | 19 | 63,050,356 | 63,193,800 | 143,445 | loss | CNVs that are Singletons |
| SK0232-003 (59838) | M | SPX | 19 | 63,483,000 | 63,771,100 | 288,100 | gain | CNVs that are Singletons |
| MM0018-003 (59980) | M | MPX | 20 | 11,319,093 | 11,424,900 | 105,808 | loss | CNVs that are Singletons |
| SK0335-003 (72815) | F | CHR | 20 | 14,955,730 | 15,011,214 | 55,485 | loss | CNVs that are Singletons |
| SK0258-004 (67930) | M | SPX | 20 | 45,468,000 | 45,673,300 | 205,300 | gain | CNVs that are Singletons |
| MM0126-003 (54581) | M | MPX | 21 | 22,839,570 | 22,938,377 | 98,808 | gain | CNVs that are Singletons |
| SK0118-003 (52027) | M | SPX | 21 | 28,060,406 | 28,250,400 | 189,995 | loss | CNVs that are Singletons |
| SK0186-004 (52964) | M | SPX | X | 22,962,800 | 23,119,000 | 156,200 | loss | CNVs that are Singletons |
| MM0087-003 (59962L) | M | MPX | X | 25,516,263 | 25,620,400 | 104,138 | loss | CNVs that are Singletons |
| NA0100-000 (70601L) | M | SPX | X | 44,395,900 | 45,060,800 | 604,901 | gain | CNVs that are Singletons |
| SK0087-003 (60692L) | F | MPX | X | 83,866,300 | 92,175,100 | 8,308,800 | loss | CNVs that are Singletons |
| MM0020-004 (47838) | M | MPX | X | 87,452,050 | 87,595,200 | 143,151 | gain | CNVs that are Singletons |
| SK0228-003 (62083) | M | SPX | X | 104,153,000 | 104,638,000 | 485,000 | gain | CNVs that are Singletons |
| SK0088-003 (64798) | M | SPX | X | 114,042,922 | 114,215,435 | 172,513 | gain | CNVs that are Singletons |
| MM0087-003 (59962L) | M | MPX | X | 130,406,000 | 130,695,499 | 289,500 | gain | CNVs that are Singletons |
| NA0016-000 (51524L) | F | SPX | X | 140,600,370 | 140,907,495 | 307,125 | gain | CNVs that are Singletons |
| SK0234-003 (64340) | M | MPX | X | 142,561,000 | 142,682,000 | 121,000 | loss | CNVs that are Singletons |
| SK0320-003 (79449) | M | SPX | X | 143,059,574 | 143,399,300 | 339,727 | gain | CNVs that are Singletons |
| SK0123-004 (60536L) | M | MPX | X | 147,974,000 | 148,479,449 | 505,449 | gain | CNVs that are Singletons |
| SK0278-003 (74431) | M | SPX | 1 | 188,543,244 | 188,935,335 | 392,092 | gain | CNVs that overlap ACRD |
| MM0149-003 (42382) | M | MPX | 1 | 191,030,551 | 191,223,110 | 192,560 | gain | CNVs that overlap ACRD |
| SK0229-003 (62211) | M | SPX | 1 | 242,451,000 | 243,113,489 | 662,489 | gain | CNVs that overlap ACRD |
| NA0016-000 (51524L) | F | SPX | 1 | 243,172,012 | 243,301,056 | 129,044 | gain | CNVs that overlap ACRD |
| MM0063-003 (46687) | F | MPX | 2 | 50,780,202 | 50,859,200 | 78,999 | loss | CNVs that overlap ACRD |
| SK0234-003 (64340) | M | MPX | 2 | 54,171,783 | 54,345,700 | 173,917 | gain | CNVs that overlap ACRD |
| SK0188-003 (53684) | M | SPX | 2 | 112,415,581 | 112,510,212 | 94,632 | loss | CNVs that overlap ACRD |
| MM0019-003 (42052) | M | MPX | 2 | 201,286,000 | 201,317,056 | 31,067 | loss | CNVs that overlap ACRD |
| MM0296-003 (47829) | M | MPX | 2 | 221,429,610 | 221,551,000 | 121,391 | loss | CNVs that overlap ACRD |
| NA0004-000 (47490) | M | SPX | 2 | 235,797,267 | 236,239,000 | 441,734 | gain | CNVs that overlap ACRD |
| MM0068-003 (60836) | M | MPX | 3 | 1,720,948 | 1,795,234 | 74,287 | gain | CNVs that overlap ACRD |
| NA0067-000 (65344L) | M | SPX | 3 | 61,075,295 | 61,581,100 | 505,806 | gain | CNVs that overlap ACRD |
| MM0296-003 (47829) | M | MPX | 4 | 328,851 | 542,862 | 214,012 | gain | CNVs that overlap ACRD |
| MM0228-004 (47602) | M | MPX | 4 | 11,820,924 | 11,983,053 | 162,130 | loss | CNVs that overlap ACRD |
| NA0129-000 (77405) | M | SPX | 4 | 38,109,899 | 38,349,444 | 239,546 | gain | CNVs that overlap ACRD |
| SK0188-003 (53664) | M | SPX | 4 | 61,408,094 | 61,758,800 | 350,707 | loss | CNVs that overlap ACRD |
| SK0057-003 (40919) | M | SPX | 4 | 74,105,760 | 74,464,300 | 358,600 | gain | CNVs that overlap ACRD |
| MM0176-003 (62118L) | M | MPX | 4 | 91,220,121 | 91,309,602 | 89,482 | loss | CNVs that overlap ACRD |
| SK0012-003 (58468L) | M | SPX | 4 | 162,387,402 | 163,362,655 | 975,254 | gain | CNVs that overlap ACRD |
| SK0012-003 (58468L) | M | SPX | 4 | 173,324,616 | 174,954,056 | 1,629,441 | gain | CNVs that overlap ACRD |
| SK0166-003 (36773) | M | SPX | 4 | 186,788,000 | 187,118,000 | 330,001 | gain | CNVs that overlap ACRD |
| SK0074-003 (60910L) | M | MPX | 4 | 188,230,567 | 190,154,000 | 1,923,434 | gain | CNVs that overlap ACRD |
| SK0083-003 (50800L) | M | CHR | 4 | 188,232,000 | 188,253,314 | 21,315 | gain | CNVs that overlap ACRD |
| MM0019-003 (42052) | M | MPX | 4 | 190,172,765 | 191,306,043 | 1,133,279 | gain | CNVs that overlap ACRD |
| SK0188-003 (53664) | M | SPX | 5 | 13,832,700 | 14,237,600 | 404,901 | gain | CNVs that overlap ACRD |
| NA0078-000 (63727) | M | MPX | 5 | 79,336,190 | 79,613,516 | 277,327 | loss | CNVs that overlap ACRE/ |
| NA0145-000 (82058L) | M | SPX | 5 | 89,445,869 | 90,172,900 | 727,032 | gain | CNVs that overlap ACRD |
| SK0167-003 (60966L) | F | MPX | 5 | 120,343,925 | 120,474,000 | 130,076 | gain | CNVs that overlap ACRD |
| NA0019-000 (64122L) | M | SPX | 5 | 120,964,000 | 121,095,213 | 131,214 | gain | CNVs that overlap ACRD |
| MM0215-004 (47095) | M | MPX | 5 | 132,619,430 | 132,732,003 | 112,574 | loss | CNVs that overlap ACRD |
| SK0073-003 (57283L) | F | CHR | 5 | 134,426,000 | 134,519,000 | 93,000 | gain | CNVs that overlap ACRD |
| SK0272-003 (70721) | F | SPX | 6 | 77,622,920 | 77,673,932 | 51,012 | loss | CNVs that overlap ACRD |
| MM0225-004 (60826) | M | MPX | 6 | 93,087,482 | 98,011,900 | 4,924,419 | gain | CNVs that overlap ACRD |
| SK0077-003 (48226) | M | SPX | 6 | 95,461,800 | 95,581,304 | 119,504 | loss | CNVs that overlap ACRD |
| SK0087-003 (40450) | M | MPX | 6 | 97,566,274 | 97,658,527 | 92,253 | loss | CNVs that overlap ACRD |
| SK0216-003 (58875) | M | SPX | 6 | 153,519,631 | 153,791,029 | 271,398 | gain | CNVs that overlap ACRD |
| NA0061-000 (60383) | M | SPX | 7 | 108,357,049 | 108,597,525 | 240,477 | loss | CNVs that overlap ACRD |
| SK0226-005 (61360) | M | SPX | 7 | 118,462,717 | 118,679,189 | 216,473 | loss | CNVs that overlap ACRD |

TABLE 3-continued

| FAM ID (DNA) | Sex | Type | Chr | start | stop | size | CNV | CNV Category |
|---|---|---|---|---|---|---|---|---|
| MM0218-004 (45553) | M | MPX | 8 | 89,598,961 | 89,678,800 | 79,840 | loss | CNVs that overlap ACRD |
| SK0210-004 (57601) | M | MPX | 9 | 28,577,800 | 29,218,800 | 641,000 | loss | CNVs that overlap ACRD |
| SK0273-003 (71182) | M | MPX | 9 | 70,739,231 | 70,870,084 | 130,854 | loss | CNVs that overlap ACRD |
| SK0118-003 (52027) | M | SPX | 9 | 111,652,000 | 112,212,452 | 560,453 | gain | CNVs that overlap ACRD |
| NA0066-000 (64119L) | M | SPX | 9 | 116,528,784 | 116,612,329 | 83,546 | loss | CNVs that overlap ACRD |
| SK0102-004 (31899) | M | SPX | 10 | 42,611,900 | 43,266,300 | 654,400 | gain | CNVs that overlap ACRD |
| SK0102-004 (31899) | M | SPX | 10 | 44,988,900 | 45,468,800 | 479,900 | gain | CNVs that overlap ACRD |
| NA0109-000 (72873) | M | SPX | 10 | 112,267,330 | 112,405,408 | 138,079 | gain | CNVs that overlap ACRD |
| SK0131-003 (39989) | F | CHR | 10 | 128,501,014 | 128,592,091 | 91,078 | gain | CNVs that overlap ACRD |
| NA0138-000 (81816L) | M | SPX | 10 | 133,285,000 | 133,604,999 | 320,000 | gain | CNVs that overlap ACRD |
| NA0113-000 (82366L) | M | SPX | 11 | 9,984,119 | 10,667,800 | 683,682 | loss | CNVs that overlap ACRD |
| SK0218-003 (60340) | F | CHR | 12 | 1,760,084 | 1,852,412 | 92,328 | loss | CNVs that overlap ACRD |
| NA0122-000 (76018L) | F | SPX | 13 | 32,965,700 | 33,137,655 | 171,956 | gain | CNVs that overlap ACRD |
| NA0117-000 (73621) | M | SPX | 13 | 42,511,458 | 42,599,200 | 87,743 | gain | CNVs that overlap ACRD |
| MM0154-003 (56678L) | F | MPX | 13 | 54,651,953 | 55,025,229 | 373,277 | gain | CNVs that overlap ACRD |
| SK0328-003 (82302) | M | SPX | 13 | 103,896,769 | 103,930,492 | 33,724 | loss | CNVs that overlap ACRD |
| MM0295-003 (46488) | M | MPX | 13 | 113,361,712 | 113,646,000 | 284,289 | gain | CNVs that overlap ACRD |
| SK0305-004 (78621) | F | SPX | 14 | 42,022,286 | 42,210,026 | 187,741 | loss | CNVs that overlap ACRD |
| SK0320-003 (79449) | M | MPX | 14 | 45,537,581 | 45,653,418 | 115,838 | loss | CNVs that overlap ACRD |
| MM0225-004 (60826) | M | MPX | 14 | 83,373,278 | 83,435,200 | 61,923 | gain | CNVs that overlap ACRD |
| MM0154-003 (56678L) | F | MPX | 14 | 106,223,861 | 106,356,482 | 132,622 | gain | CNVs that overlap ACRD |
| NA0064-000 (63582L) | M | SPX | 15 | 82,573,421 | 83,631,697 | 1,058,276 | loss | CNVs that overlap ACRD |
| MM0256-004 (46991) | M | MPX | 15 | 87,922,400 | 87,993,909 | 71,510 | gain | CNVs that overlap ACRD |
| SK0266-003 (68257) | M | SPX | 16 | 6,813,789 | 0,898,849 | 85,060 | loss | CNVs that overlap ACRD |
| NA0063-000 (60351) | M | SPX | 16 | 73,397,667 | 73,657,067 | 259,400 | loss | CNVs that overlap ACRD |
| NA0095-000 (75414L) | M | SPX | 16 | 74,576,356 | 74,613,000 | 36,645 | loss | CNVs that overlap ACRD |
| SK0284-003 (72687) | F | SPX | 17 | 28,985,300 | 29,960,700 | 975,400 | gain | CNVs that overlap ACRD |
| SK0012-003 (58468L) | M | SPX | 18 | 27,565,032 | 27,781,900 | 216,869 | gain | CNVs that overlap ACRD |
| SK0152-003 (41548L) | M | CHR | 18 | 32,174,061 | 32,990,975 | 816,914 | loss | CNVs that overlap ACRD |
| SK0147-003 (47544L) | F | SPX | 18 | 37,509,556 | 37,950,450 | 440,895 | gain | CNVs that overlap ACRD |
| SK0304-003 (78063) | M | SPX | 18 | 46,101,841 | 46,218,000 | 116,160 | gain | CNVs that overlap ACRD |
| NA0138-000 (81816L) | M | SPX | 18 | 69,282,461 | 69,330,584 | 48,124 | loss | CNVs that overlap ACRD |
| SK0023-003 (58096) | M | SPX | 21 | 46,497,675 | 46,678,820 | 181,145 | gain | CNVs that overlap ACRD |
| NA0112-000 (72340) | M | SPX | X | 38,250,331 | 38,371,333 | 121,003 | gain | CNVs that overlap ACRD |
| SK0283-003 (72309) | F | CHR | 4 | 44,762,996 | 44,858,504 | 95,508 | gain | CNVs that overlap ACRD |
| MM0010-005 (47372) | M | MPX | 4 | 44,773,367 | 44,846,800 | 73,434 | gain | CNVs that overlap ACRD |
| NA0093-000 (66999) | M | SPX | 4 | 44,773,367 | 44,846,800 | 73,433 | gain | CNVs that overlap ACRD |
| MM0109-003 (46486) | F | SPX | 4 | 189,538,747 | 189,825,000 | 286,254 | gain | CNVs that overlap ACRD |
| SK0112-003 (46100) | M | MPX | 4 | 189,580,553 | 190,228,000 | 647,447 | gain | CNVs that overlap ACRD |

Figure 3:
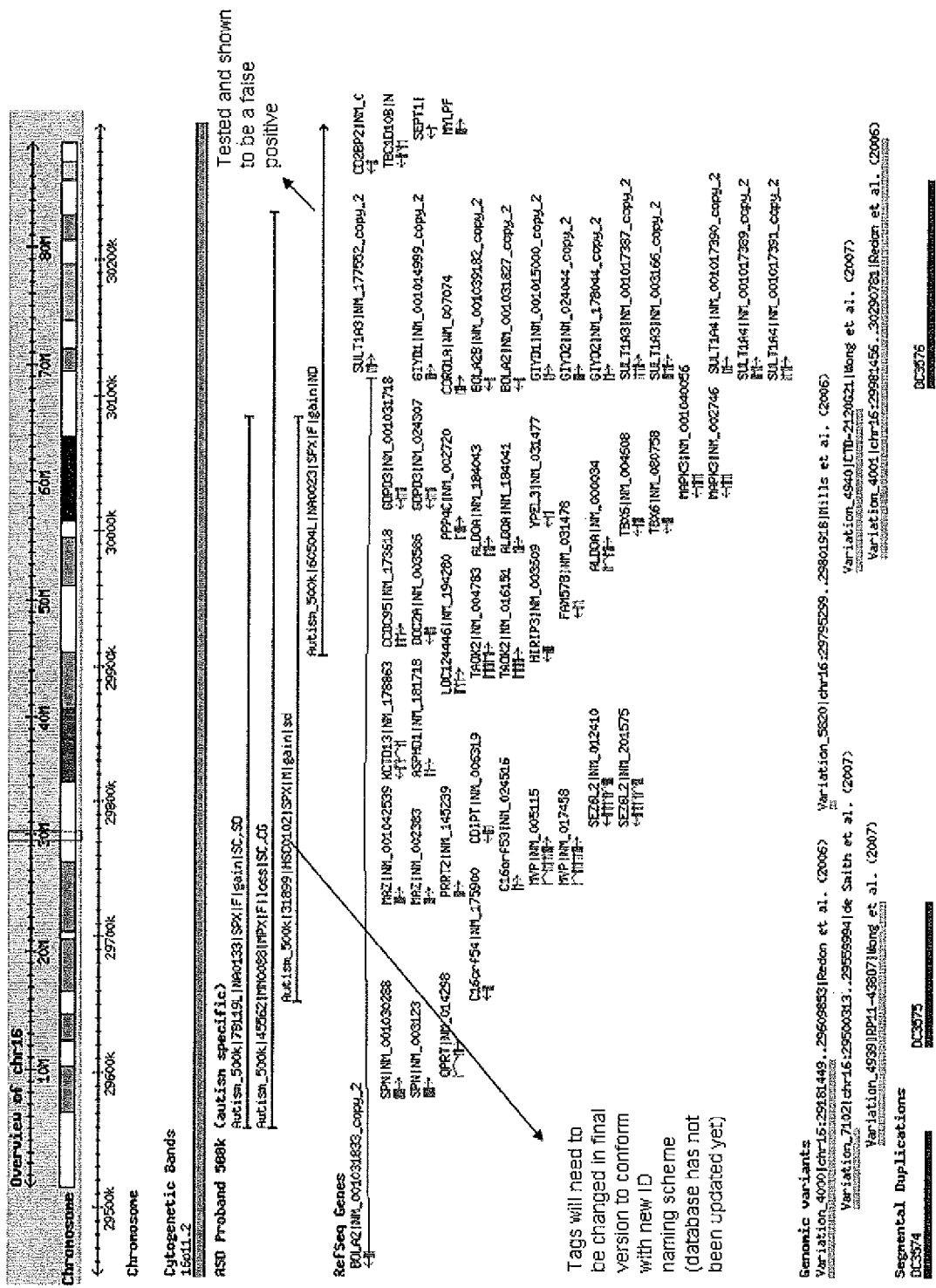
FIG. 3 illustrates the chromosome 16p11.2 region as depicted in the Autism Chromosome Rearrangement Database.

Wide-ranging prevalence frequencies of cytogenetically detectable chromosomal abnormalities in ASD, and the inability of microarray scans to find balanced abnormalities, prompted karyotyping to be performed. Karyotyping (and FISH) also provided the ability to characterize the chromosomal context (e.g. ring chromosomes) of some of the CNV regions, something not possible using microarrays alone. Therefore, 313 unbiased idiopathic cases where blood was available were examined and 5.8% (18/313) cases were found to have balanced (11) or unbalanced (7) karyotypes (all unbalanced karyotypic changes (7) were also found by microarray analysis and are included in the CNV statistics). The genomic characteristics of all CNVs are shown in the Autism Chromosome Rearrangement Database (see FIG. 3). In this study, CNV loss and gain will typically equate to a standard deletion or duplication. In some cases a duplication of only part of a gene could lead to its disruption (Table 5), and there are also positional effects on gene expression to consider.

De Novo, Overlapping/Recurrent, and Inherited Structural Variants

Structural variants found in ASD cases were initially prioritized to possibly be etiologic if they were not in controls and, (i) de novo in origin (25 cases) (see Table 5 below), (ii) overlapping (27 cases at 13 loci) in two or more unrelated samples (see Table 7 below), (iii) recurrent (same breakpoints) in two or more unrelated samples (four cases at two loci), (iv) or inherited (the remainder). In a proof of principle analysis, CNVs were found at known ASD loci: NLGN4 and 22q, 15q, SHANK3 and NRXN1 in categories i, ii, iii, and iv, respectively. ASD structural variants found in controls (eg. NRXN1) could also be involved.

TABLE 5

De Novo Rearrangements in ASD cases

| | FamID (DNA)[1] | Sex | Type | Chromosome[2] | Size (bp)[3] | CNV | Genes[4] | Phenotype Comments[5] |
|---|---|---|---|---|---|---|---|---|
| 1 | SK0181-004 (52191) | M | CHR (SPX) | 3p14.1-3p13 (a) | 5,346,900 | loss | 13 genes | IQ = 107 |
| | | | | t(6:14)(q13:q21) (k) | N/A | none | 11 genes | Dysmorphology |
| 2 | SK0152-003 (41548) | M | CHR (MPX)[6] | 3p25.1-p24.3 (a) | 1,409,600 | loss | 12 genes | IQ = unknown |
| | | | | 5p15.31-p15.2 (a) | 3,429,389 | loss | 8 genes | |
| | | | | 12q12 (a) | 422,842 | loss | 4 genes | |
| | | | | t(5:7)(p15p13) (k) | N/A | none | CDH18 | |
| 3 | SK0215-006 (58449) | M | CHR (SPX) | 1p21.3 (a) | 1,092,500 | loss | DPYD whole | IQ = 38, SLI |

TABLE 5-continued

De Novo Rearrangements in ASD cases

| | FamID (DNA)[1] | Sex | Type | Chromosome[2] | Size (bp)[3] | CNV | Genes[4] | Phenotype Comments[5] |
|---|---|---|---|---|---|---|---|---|
| 4 | SK0205-004 (56242) | F | CHR (SPX) | 5p15.33-5p15.2 (k) | 13,800,984 | loss | 46 genes | IQ = unknown, Cri du chat |
| 5 | SK0083-003 (50800) | M | CHR (SPX) | 7q31.1-q31.31 (k) | 11,023,507 | loss | 25 genes | IQ = 76 |
| 6 | SK0131-003 (39989) | F | CHR (SPX) | 7q31.1-q32.2 (k) | 15,486,722 | loss | >50 genes | IQ = 95, SLI |
| 7 | SK0243-003 (67941) | M | CHR (SPX) | 15q23-q24.2 (k) | 4,289,500 | loss | >50 genes | IQ = unknown, SLI |
| 8 | SK0073-003 (57283) | F | CHR (SPX) | 15q11.2-q13.3 (k) | 11,922,600 | gain | >50 genes | IQ = unknown |
| 9 | SK0245-005 (68517) | M | CHR (SPX) | 15q11.2-q13.3 (k) | 11,871,747 | gain | >50 genes | IQ = unknown |
| 10 | SK0218-003 (60340) | F | CHR (MPX)[4] | 18q21.32-18q23 (k) | 20,358,999 | loss | >50 genes | IQ = unknown, seizures, dysmorphology |
| 11 | NA0039-000 (69736) | F | CHR (SPX) | 22q13.31-q13.33 (k) | 3,231,700 | loss | 41 genes | IQ = unknown |
| 12 | NA0097-000 (82361) | F | CHR (SPX) | Xp22.33-p22.31 (a) | 5,825,311 | loss | 21 genes + NLGN4 | IQ = unknown |
| 13 | SK0283-003 (72309) | F | CHR (SPX) | 47, XX, ring chr1 (k) | N/A | gain | >50 genes | IQ = 38 |
| 14 | SK0133-003 (46012) | M | CHR (SPX) | t(5:8:17)(q31.1:q24.1:q21.3) (k) | N/A | none | 5 genes | IQ = unknown |
| 15 | NA0002-000 (52026) | M | SPX | 7q36.2 (a) | 66,462 | loss | DPP6 exonic | IQ = unknown |
| 16 | SK0262-003 (68609) | M | SPX | 8p23.3 (a) | 791,089 | gain | DLGAP2 exonic | IQ = unknown |
| 17 | MM0278-003 (57788) | M | SPX | 12q24.21-q24.33 (a) | 18,218,000 | gain | >50 genes | IQ = 36 |
| 18 | NA0067-000 (65344) | M | SPX | 16q24.3 (a) | 265,667 | loss | ANKRD11 exonic | IQ = unknown |
| 19 | MM0088-003 (45562) | F | MPX | 16p11.2 (a) | 675,829 | loss | 28 genes | IQ = 87 |
| 20 | SK0102-004 (31899) | M | SPX | 16p11.2 (a) | 432,600 | gain | 24 genes | IQ = 74, Epilepsy |
| 21 | SK0244-003 (69183) | M | SPX | 21q22.3 (a) | 353,936 | gain | 4 genes | IQ = 80 |
| 22 | MM0109-003 (46486) | F | SPX | 20q13.33 (a) 22q13.33 (a) | 1,427,661 276,702 | gain loss | 44 genes 13 genes + SHANK3 | IQ = unknown |
| 23 | SK0119-003 (35190) | M | MPX[4] | 22q11.21 (a) | 2,771,300 | loss | >50 genes | IQ = 58, VCF syndrome |
| 24 | SK0297-003 (76066) | M | SPX-MZ | 22q11.21 (a) | 4,281,262 | gain | >50 genes | IQ = 107, dysmorphology |
| 25 | SK0306-004 (78681) | F | SPX | Xp11.23-11.22 (a) | 4,643,367 | gain | >50 genes | IQ = 87 |

[1]Table is sorted based on family type. Probands with abnormal karyotypes (CHR) (1-14) are separated from probands belonging to simplex (SPX) and multiplex (MPX) families with normal karyotypes(15-25).
[2]De novo event detected by either karyotype (k) or microarray (a)
[3]De novo CNV/translocation has been confirmed by at least one of karyotype, FISH, or qPCR. CNV size is based on array results. The breakpoints have not been accurately defined, and CNVs may be smaller or larger than posted.
[4]When only a single gene is involved if the CNV intersects (suggesting it may disrupt the gene) the term 'exonic' is used and if the CNV encompasses the entire gene the term 'whole' is used.
[5]For multiplex families the de novo events were not detected in affected siblings.
**comment on case 25 that is also in Table 3 (see entry #2

TABLE 6

Recurrent and overlapping loci in ASD

| | Chromosome | FamID (DNA) | Sex | Type[1] | Size (bp)[2] | CNV | Origin | Genes[3] | Phenotype Comments |
|---|---|---|---|---|---|---|---|---|---|
| 1 | 2q14.1 | SK0147-003 (47544) | F | SPX | 478,370 | loss | Paternal | DPP10 exonic | IQ = unknown, NF1 |
| | | SK0288-003 (75420) | F | SPX-MZ | 105,120 | gain | Paternal | DPP10 intronic | IQ = 83 |
| 2 | 2q32.1 | SK0306-004 (78681) | F | SPX | 97,130 | loss | Unknown | None | IQ = 87 |
| | | NA0030-000 (55240) | M | SPX | 112,323 | loss | Unknown | None | IQ = unknown |
| 3 | 6q22.31 | MM0220-003 (61180) | M | MPX | 318,000 | gain | Paternal | PLN, c6orf204 whole | IQ = unknown |
| | | NA0025-000 (60490) | M | SPX | 293,989 | gain | Paternal | PLN, c6orf204 whole | IQ = unknown |
| 4 | 7q36.2 | SK0190-003 (54742) | M | SPX | 1,780,000 | gain | Maternal | DPP6 whole | IQ = 82 |
| | | SK0115-003 (40555) | M | SPX | 274,000 | gain | Unknown | DPP6 exonic | IQ = unknown |
| | | SK0058-003 (59963) | M | MPX | 16,788 | gain | Maternal | DPP6 intronic | IQ = 111 |
| | | NA0002-000 (52026) | M | SPX | 66,462 | loss | De novo | DPP6 exonic | IQ = unknown |
| 5 | 8q11.23 | SK0143-003 (36812) | M | SPX | 285,200 | gain | Unknown | UNQ9433 whole, RB1CC1 exonic | IQ = 66 Apraxia, CHD, Seizures |
| | | MM0236-004 (46475) | M | MPX | 271,679 | gain | Unknown | RB1CC1 exonic | IQ = 99 |

TABLE 6-continued

Recurrent and overlapping loci in ASD

| | Chromosome | FamID (DNA) | Sex | Type[1] | Size (bp)[2] | CNV | Origin | Genes[3] | Phenotype Comments |
|---|---|---|---|---|---|---|---|---|---|
| 6 | 9p24.1 | SK0270-003 (71341) | M | SPX | 38,900 | loss | Unknown | none | IQ = 91, SLI |
| | | MM0103-003 (42387) | M | MPX | 34,950 | loss | Paternal | none | IQ = 107 |
| 7 | 11p12 | MM0272-003 (45563) | M | MPX | 262,938 | loss | Maternal | none | IQ = 111, Seizures |
| | | SK0167-003 (60966) | F | MPX | 192,846 | loss | Unknown | none | IQ = 91 |
| 8 | 13q21.32 | SK0023-003 (58096) | M | SPX | 189,438 | gain | Unknown | PCDH9 intronic | IQ = 91, Seizures |
| | | MM0299-003 (51674) | F | MPX | 172,401 | gain | Paternal | PCDH9 intronic | IQ = 39 |
| 9 | 15q11.2-q13.3 | SK0073-003 (57283) | F | CHR | 11,922,600 | gain | De novo | >50 genes | IQ = unknown |
| | | SK0245-005 (68517) | M | CHR | 11,871,747 | gain | De novo | >50 genes | IQ = unknown |
| 10 | 16p12.1 | MM0109-003 (46486) | F | SPX | 1,246,288 | gain | Maternal | 8 genes | IQ = unknown |
| | | MM0289-003 (42267) | M | MPX | 802,555 | loss | Maternal | 5 genes | IQ = 63 |
| 11 | 16p11.1 | NA0133-000 (78119) | F | SPX | 525,319 | gain | Maternal | 29 genes | IQ = unknown |
| | | SK0102-004 (31899) | M | SPX | 432,600[4] | gain | De novo | 24 genes | IQ = 64, Epilepsy |
| | | MM0088-003 (45562) | F | MPX | 675,829 | loss | De novo | 32 genes | IQ = 87 |
| 12 | 22q11.2 | SK0119-003 (35190) | M | MPX | 2,771,300 | loss | De novo | >50 genes | IQ = 58, VCF syndrome |
| | | SK0091-004 (46407) | F | MPX | 4,281,262 | gain | Paternal | >50 genes | IQ = 126 |
| | | SK0297-003 (76066) | M | SPX-MZ | 4,281,262 | gain | De novo | >50 genes | IQ = 107, dysmorphology |
| | | SK0323-003 (80022) | M | MPX | 743,100 | gain | Unknown | 7 genes | IQ = unknown |
| 13 | 22q13.31 | SK0123-004 (60536) | M | MPX | 601,528 | gain | Maternal | none | IQ = 93 |
| | | MM0102-003 (47598) | M | MPX | 80,380 | loss | Maternal | none | IQ = 70 |

Figure 2:
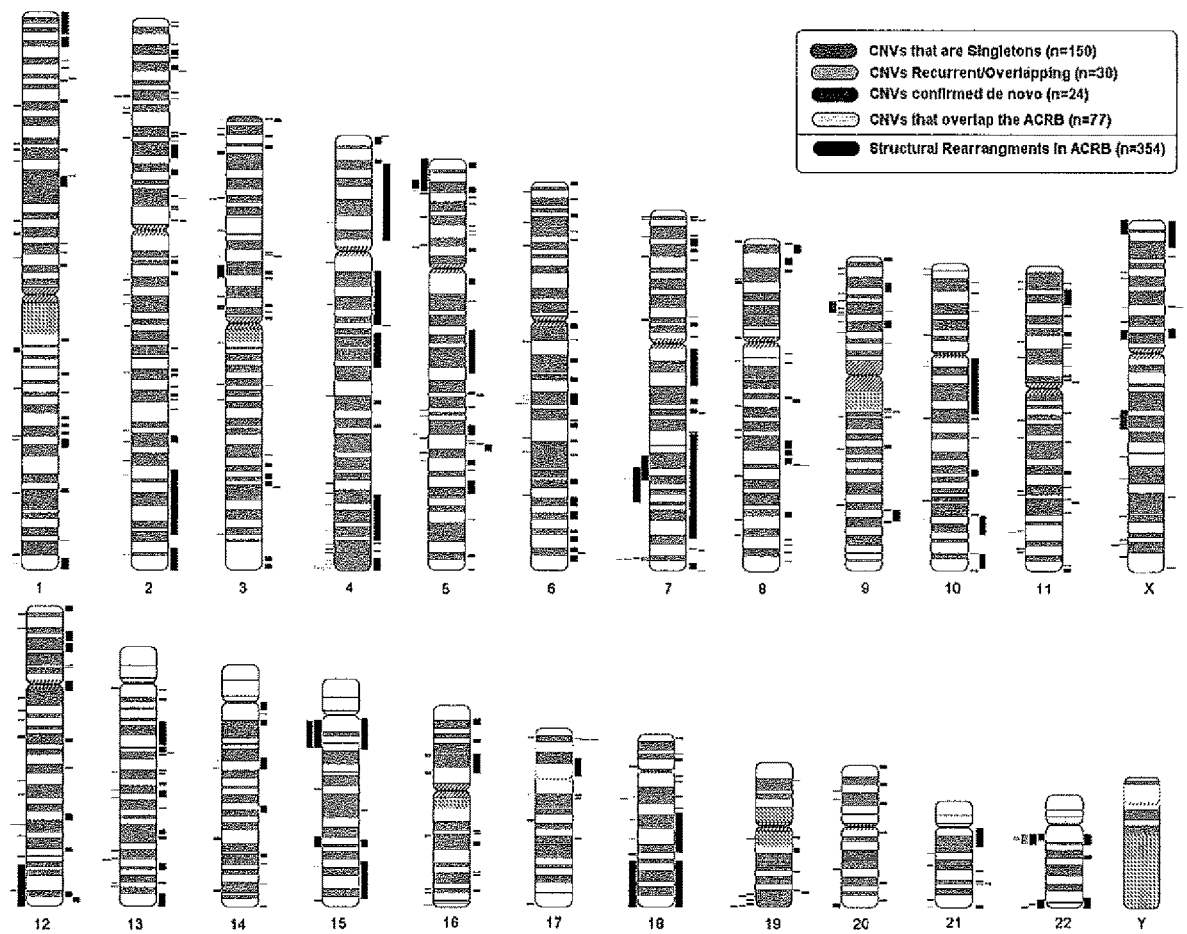
FIG. 2 illustrates a genome-wide distribution of ASD-specific CNVs as described in Table 3.

[1]Families are grouped based on simplex (SPX), multiplex (MPX) and chromosomal abnormalities (CHR). Simplex families with affected monozygotic twins is denoted as SPX-MZ. The de novo cases also appear in Table 2 and some of the family pedigrees are shown in FIG. 2 and Supplemental FIG. 2.
[2]CNV size is based on array results. The breakpoints have not been accurately defined, and CNVs may be smaller or larger than posted.
[3]When only a single gene is involved if the CNV intersects (suggesting it may disrupt the gene) the term 'exonic' is used and if the CNV encompasses the entire gene the term 'whole' is used.
[4]CNV is only called by one algorithm By testing parental DNA and validating CNVs, a de novo mutation rate of 7.1% (4/56) and 2.0% (1/49) was observed in idiopathic simplex and multiplex families, respectively. There was parental information for 13 of 18 cases discovered to carry cytogenetic abnormalities and 7 (6 simplex, 1 multiplex) of these were de novo in origin. Since only 1/7 (from a simplex family) of these was balanced and directly interrupting a gene, it was estimated that this class of rearrangements had much less of a contribution than CNVs to the total rate of de novo and structural variation in the present cohort.

The collective data identified 25 de novo cases (Table 5) and in three, two or more events were identified. Notably, in family SK0152 (FIG. 4a) there were four de novo events. In MM019 (FIG. 4b) there were two de novo deletions, one leading to haplo-insufficiency of SHANK3.

The 13 loci where overlapping ASD-specific CNVs were found are likely indicative of ASD-susceptibility since they arise in two or more unrelated families. In six, gains and losses often encompassing entire genes were observed at the same locus (Table 6) suggesting general gene dysregulation to be involved.

Using q-PCR or by assessing SNP patterns, 196 inherited CNVs (90 maternal and 106 paternal) were confirmed. No sub-grouping of these demonstrated obvious parent-of-origin effects (the two chromosome 15q11-q13 duplications detected were both de novo in origin). A 160 kb deletion was detected in a male inherited from a carrier mother, leading to a null PTCHD1 in the proband and his dizygotic twin brother (FIG. 4c). There were also instances where apparently balanced inherited translocations were accompanied by de novo deletions in the offspring (eg. DPYD) (FIG. 4d).

Candidate ASD-Susceptibility Genes and Loci Identified

New ASD candidates identified were those with a structural change (either de novo or found in two or more unrelated ASD cases, or for the X chromosome an allele being transmitted maternally from an unaffected carrier) specific to that gene, including ANKRD11, DLGAP2, DPP6, DPP10, DPYD, PCDH9 and PTCHD1 (Tables 5 and 6). As previously noted, NLGN4, SHANK3 and NRXN1 were also identified. The PCDH9 and NRXN1 genes are also found as CNVs in controls in the DGV (Database of Genomic Variants).

Additional positional candidate genes identified were those found interrupted by balanced cytogenetic breakpoints including NEGR1, PIP5K1B, GABRG1, KLHL3, STK3, ST7, SATB2 (Table 1). Moreover, 77 CNVs in the stringent dataset overlapped with the Autism Chromosome Rearrangement Database providing a second line of evidence for involvement (FIG. 2). For example, a 4.6 Mb de novo duplication at Xp11.23-11.22 was detected in a female SK0306-004 (Table 5) and a male in the database.

DPP6 and DPP10 emerge as being positional and functional candidates. DPP6 (~1.5 Mb in size at 2q14.1) and DPP10 (~1.3 Mb at 7q36.2) code for accessory transmembrane dipeptidyl peptidase-like subunits that affect the expression and gating of Kv4.2 channels (KCND2). Kv4.2 channels function in regulation of neurotransmitter release and neuronal excitability in the glutamatergic synapse at the same sites where SHANK3 and the NLGN gene products are found. In addition, autism balanced breakpoints have been mapped near KCND2 at 7q31.

Figure 4:
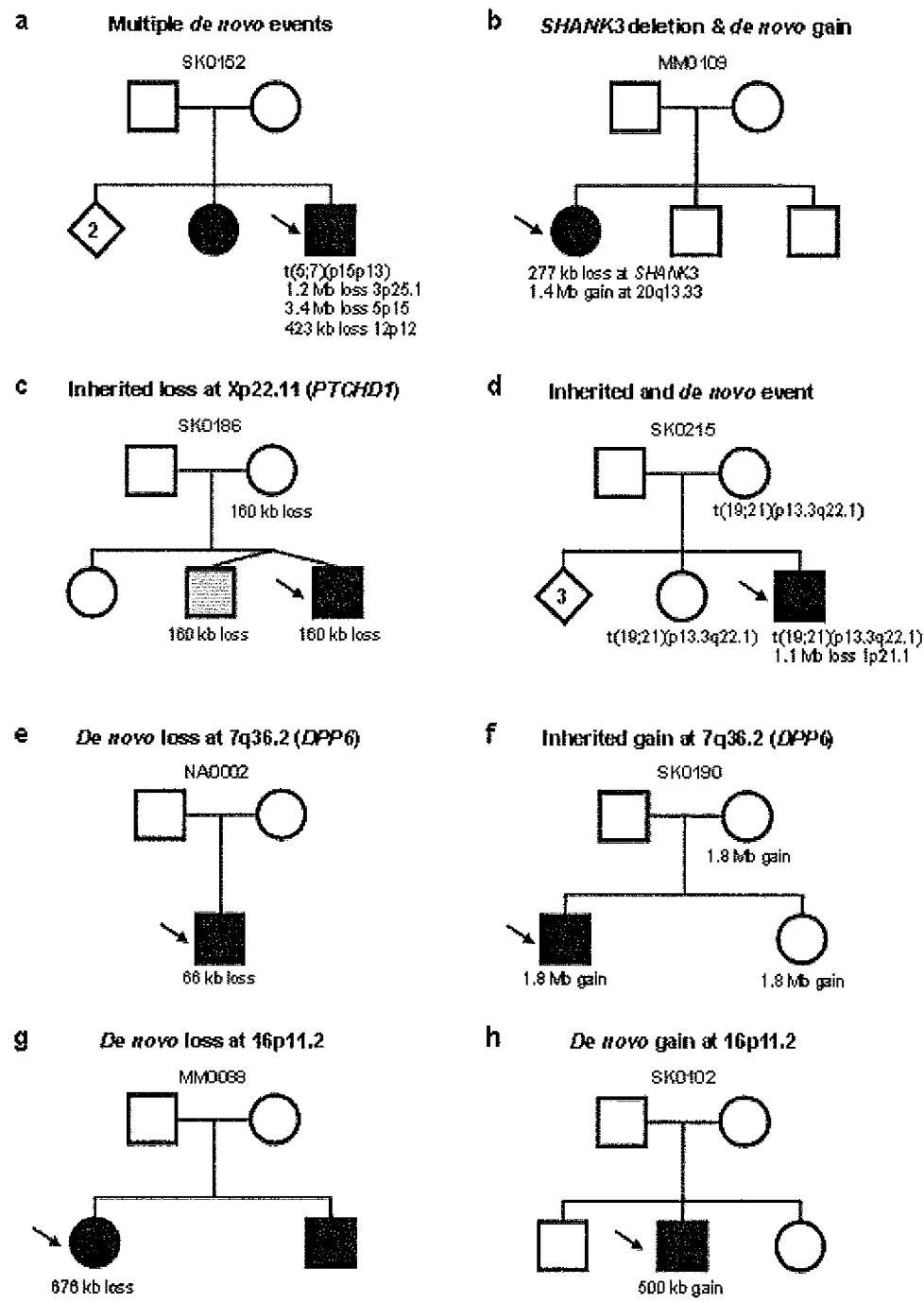
FIG. 4 illustrates examples of CNVs observed in ASD families including probands having multiple de novo events (a); rearrangements in the SHANK3 gene (b); probands with chromosome X deletions (at PTCHD1) from female carriers (c) or inherited translocations in addition to an unrelated de novo deletion (d); overlapping events in unrelated probands either de novo (e) or inherited (f) at the DPP6 locus; and recurrent de novo events at chromosome 16p11.2 in unrelated probands either gains (h) or losses (g)
Figure 5:
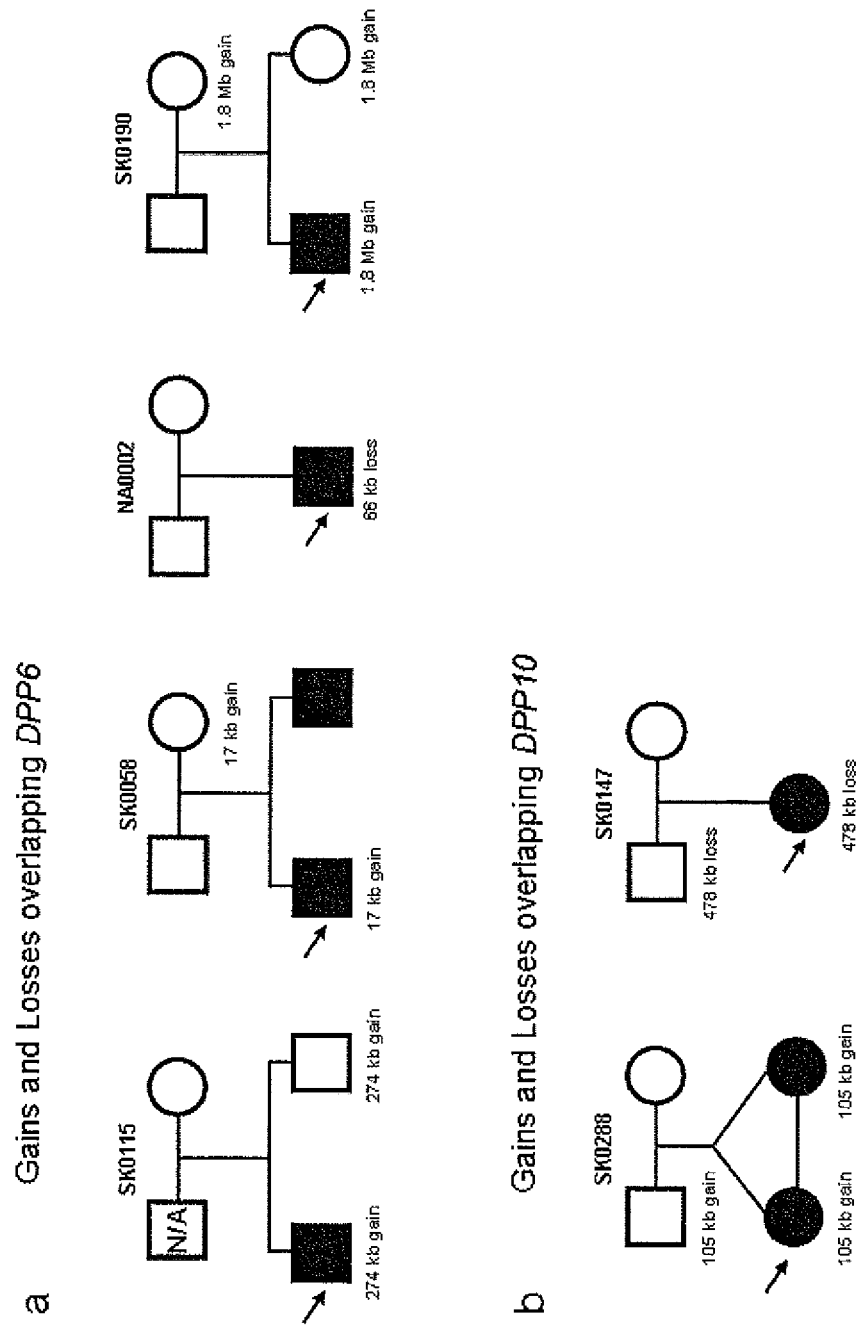
FIG. 5 illustrates examples of DPP6 and DPP10 ASD-related CNVs.

For DPP10 there are inherited CNV gains and losses (Table 5, FIG. 4). De novo and inherited CNVs were found at the multi-transcript DPP6 gene. A 66 kb de novo loss encompassing exons 2 and 3 is found in a male in family NA0002 (FIG. 4e). In family SK0190, the male proband and an unaffected female sibling both carry a CNV gain inherited from an unaffected mother (FIG. 4f) that encompassed the entire DPP6. A 270 kb gain was found in SK0115-003 that extends across the first exon (which may disrupt the functional gene) and SK0058-003 carries a maternally-inherited 16 kb intronic CNV gain (Table 1; FIG. 5).

Medical Genetics

Structural variants overlapping loci involved in medical genetic conditions including Waardenburg Type IIA (3p14.1), speech and language disorder (7q31), mental retardation (MRX15q23-q24, 16 µl 1.2) and velocardialfacial syndrome (VCFS) (22q13) were identified (Table 5), amongst others. Identification of the structural variant at these loci led to clinical re-assessment and either identification or refinement of the diagnosis, for additional syndromic features. Other instances (eg. SK0186-PTCHD1 deletion) (FIG. 4c) prompted re-testing of the entire family and eventually a diagnosis of mild-ASD in a previously undiagnosed sibling. This family was then redesignated multiplex as opposed to simplex.

Figure 6:
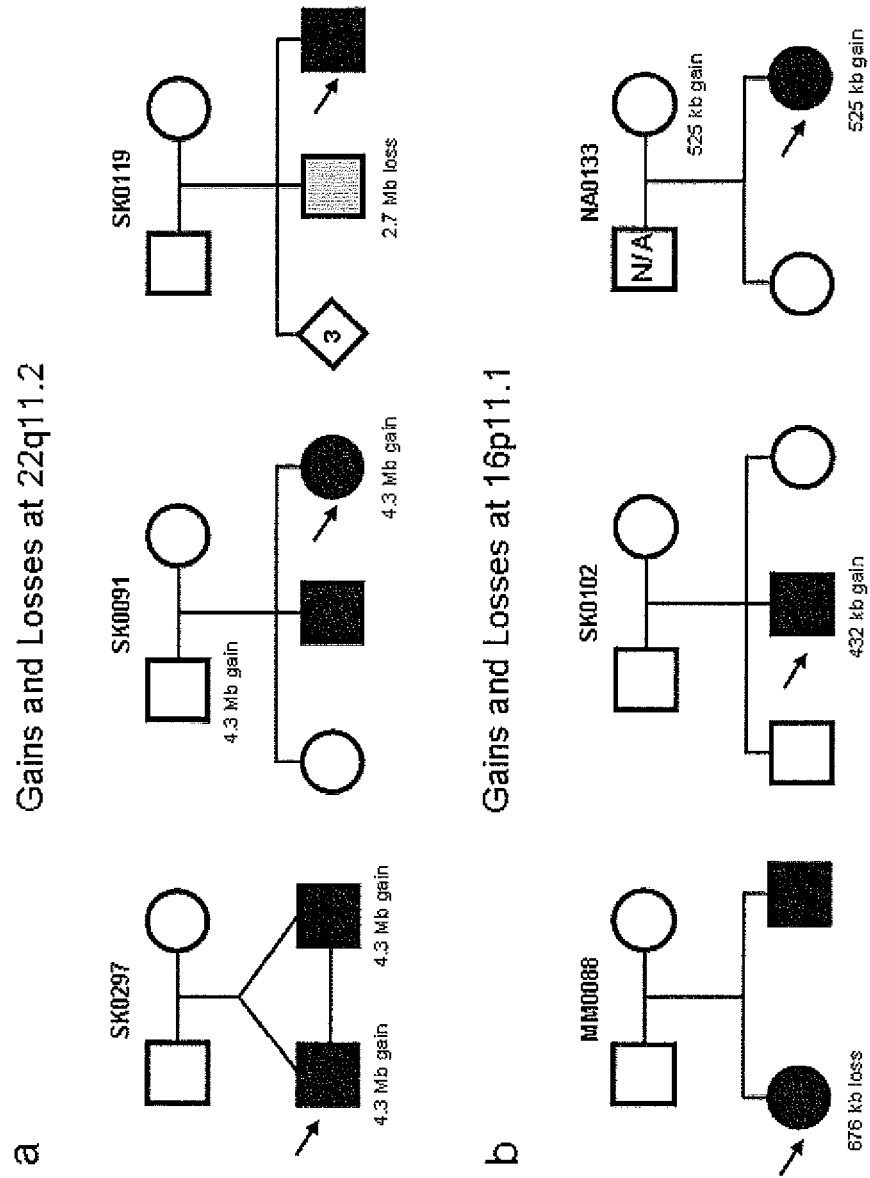
FIG. 6 illustrates examples of chromosome 22q11.2 and 16p11.2 ASD-related CNVs.

The identification of a de novo deletion (2.7 Mb) at 22q11.2 in two ASD brothers led to their re-examination and diagnosis for VCFS. The re-testing also further defined the siblings to be at opposite ends of the ASD spectrum (FIG. 6). Larger duplications (4.3 Mb) of this same region in two other ASD families (SK0289 and SK0091) did not cause VCFS (Table 6); however, in SK0091 the variant was inherited from a normal father and not found in an affected male sibling.

A recurrent ~500 kb duplication at 16p11.2 in two ASD families (SK0102 and NA0133) (FIGS. 4 and 5) was also discovered. As with DPP6/DPP10 and 22q11.2, there were carriers of these structural variants without ASD. In a third family (MM0088), the proband has a larger 676 kb de novo deletion and it is only detected in one of two ASD siblings. (FIG. 4g).

In sum, using the genome-wide scanning approach, numerous new putative-ASD loci (Tables 4 and 5, FIG. 2) were identified. Generally, ASD loci include (i) those that contain genes functioning in the PSD, (ii) and/or chromosomal regions previously shown to be involved in mental retardation, and (iii) involve dysregulation of gene expression.

CNVs that implicate ASD loci include the SHANK3, NLGN, and NRXN1-PSD genes and also identify novel loci at DPP6 and DPP10 (amongst others including PCDH9, RPS6KA2, RET from the full dataset) were identified.

Lastly, six unrelated ASD cases were identified (Table 6) that had either CNV gains or losses at the same locus which indicate that gene expression of genes in these regions are related to the development of speech and language and/or social communication in humans, as in SHANK3 and genes in the Williams-Beuren syndrome locus.

Example 2—PTCHD1 as a Marker of ASD

As set out above, a genome scan with Affymetrix 500K SNP Arrays was used to identify a CNV deletion on chromosome Xp22.11 that spans exon 1 of the PTCHD1 gene. Exon 1 is shown bolded in FIG. 7 spanning nucleotide positions 1-359. The Cdna sequence of the PTCHD1 gene (NM_173495) as well as the amino acid sequence of the corresponding encoded protein is illustrated in FIG. 7 which illustrates a genomic size of: 59325, an exon/coding exon count of 3 encoding a protein of 783 amino acids.

The deletion was determined to be an ~156 kb deletion on Xp22.11 on a male proband. The physical position of this CNV is chrX: 22,962,800-23,119,000 (UCSC 2004 Assembly). The deletion is flanked by SNP probes rs7055928 and rs1918560 (at 22.956 and 23.133 Mb from the Xp terminus, respectively). The most proximal and distal SNPs (from the Affymetrix SNP microarrays) within the deleted region, as determined by the SNP microarray analysis, are rs7879064 (23.119 Mb) and rs4828958 (22.972 Mb). PCR amplicons from within the deleted region were used to confirm the deletion by Qpcr (PCR primers and locations are given below). This deletion spans the entire exon 1 of the PTCHD1 gene (NM 173495). Analysis of both Sty and Nsp chips data identified this event and was further validated using PCR and QPCR techniques. The following primers were used:

```
PTCHD-CNV1F
                                  (SEQ ID NO: 1)
ATTCGCAGTTCCTTCGTCTT

PTCHD-CNV1R
                                  (SEQ ID NO: 2)
AAAGTGGATTGATCGGTTCC

PTCHD-CNV2F
                                  (SEQ ID NO: 3)
GCTTGAGGACGTGTTTCTCC

PTCHD-CNV2R
                                  (SEQ ID NO: 4)
CTAGGAGAGGTGGCGCTCT
```

This CNV is autism specific as it was not present in the Database of Genomic Variants (DGV) and in other controls. Furthermore, the segregation of this deletion was characterized in family and it was identified that the deletion was transmitted from a heterozygous mother. A male sibling also had language deficits.

Mutation screening of PTCHD1 in N=400 autism patients was conducted in the usual manner. The following primers were used:

```
PTCHD1-x1F
                                  (SEQ ID NO: 5)
AGCGTGCGCCTCGCCCT

PTCHD1-x1R
                                  (SEQ ID NO: 6)
TCCTTGTCCAGGAGGCTGGGA

PTCHD1-x1Bf
                                  (SEQ ID NO: 7)
GCGCCCGCTCTGCTCTA

PTCHD1-x1Br
                                  (SEQ ID NO: 8)
TCCTTGTCCAGGAGGCTGGGA

PTCHD1-x2-F
                                  (SEQ ID NO: 9)
GAATGTCCACCCTCTCCAAA

PTCHD1-x2-R
                                  (SEQ ID NO: 10)
AAGGCTACTCCTGGCCTTTT

PTCHD1-x3a-F
                                  (SEQ ID NO: 11)
CTTTGACCCAGTAGTCCCTCA

PTCHD1-x3a-R
                                  (SEQ ID NO: 12)
GCACAAACCCCTTGGTGTA

PTCHD1-x3b-F
                                  (SEQ ID NO: 13)
TGTGATTGGGTTTTACATATATGAGTC

PTCHD1-x3b-R
                                  (SEQ ID NO: 14)
AGGTCAGATTTGAAGGCACAG

PTCHD1-x3c-F
                                  (SEQ ID NO: 15)
AAAAATGCCCTGGAAGTGC

PTCHD1-x3c-R
                                  (SEQ ID NO: 16)
TGTGTGAATTCTCATAACAACTCCT
```

The mutation screening revealed an 1173V mutation.

Example 3—Identification of Additional Markers of ASD

Figure 8:
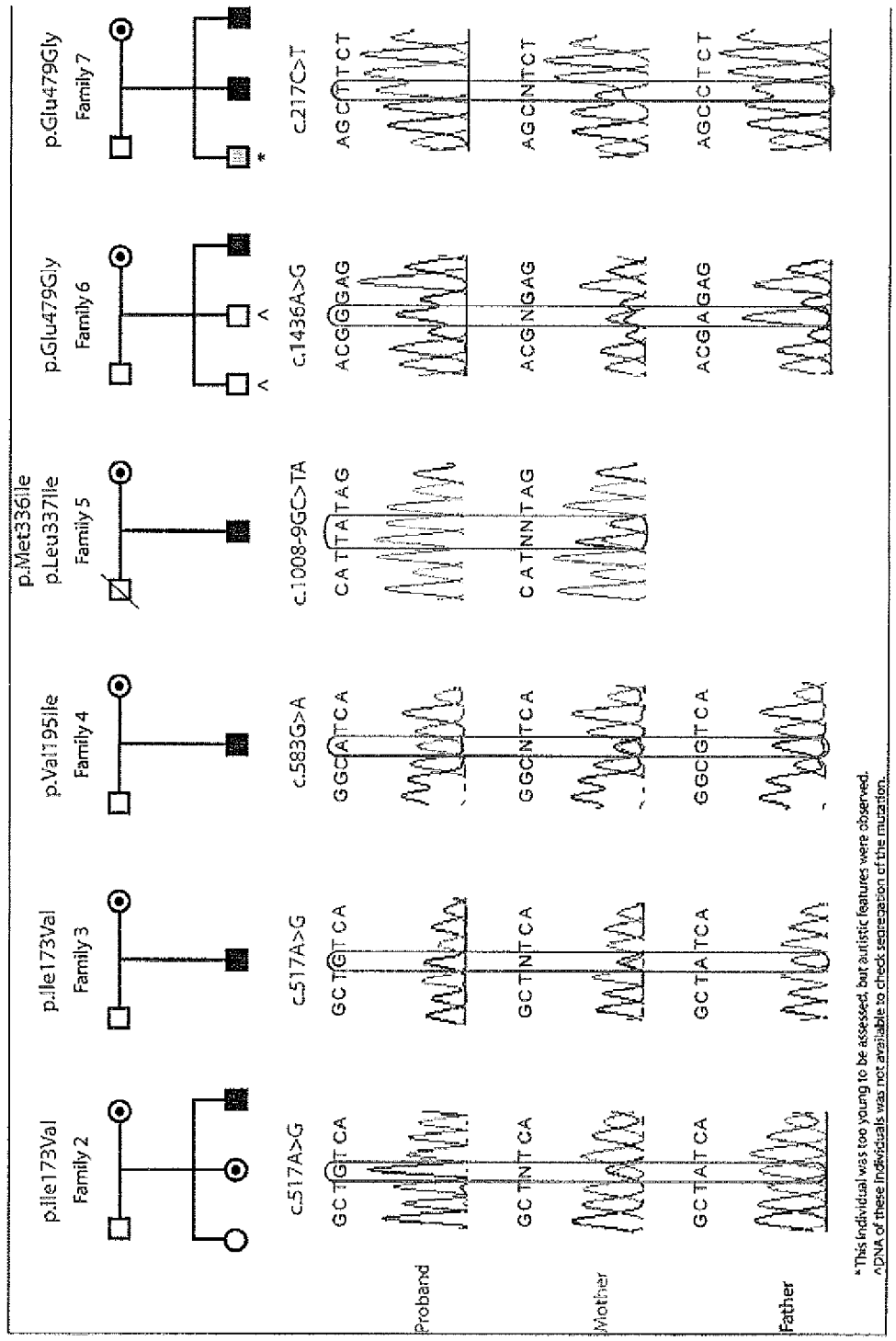
FIG. 8 illustrates ASD-related missense mutations identified in Table 7.

By sequencing the entire coding region of PTCHD1 in 900 unrelated ASD cases, six missense mutations were identified in six unrelated ASD probands (Table 7, FIG. 8). For clinical details see Table 8.

TABLE 7

| Subject ID | Exon | Mutation | Nucleotide | Sex of Proband | Transmission | Family Type | XCI Status of Carrier Mother | Population Ancestry | Frequency in ASD | No. of Cont Chromosomes Test |
|---|---|---|---|---|---|---|---|---|---|---|
| Family 1 | 1 | 167-kb deletion, disrupts PTCHD1 gene at Xp22.11 | | M | Mother | Multiplex | Skewed | European | 1 in 427 | 2067 (M = 769 F = 1298) |
| Family 1 | 1 | 167-kb deletion, disrupts PTCHD1 gene at Xp22.11 | | M | Mother | Multiplex | Skewed | European | 1 in 427 | 2067 (M = 769 F = 1298) |
| Family 2 | 2 | I173V | 517A > G | M | Mother | Multiplex | Random | European\Mixed | 2 in 900 | 659 (M = 219 F = 220) |
| Family 3 | 2 | I173V | 517A > G | M | Mother | Simplex | Random | European | 2 in 900 | 659 (M = 219 F = 220) |
| Family 4 | 2 | V195I | 583G > A | M | Mother | Simplex | NC | European | 1 in 900 | 659 (M = 219 F = 220) |
| Family 5 | 2 | ML336-7II | 1008-9GC > TA | M | Mother | Simplex | Random | Asian | 1 in 900 | 751* (M = 249 F = 251) |
| Family 6 | 3 | E479G | 1436A > G | M | Mother | Multiplex | Random | European | 1 in 900 | 427 (M = 137 F = 145) |
| Family 7 | 1 | L73F | 217C > T | M | Mother | Multiplex | NC | Not Available | 1 in 900 | 427 (M = 137 F = 145) |

*Out of 751 control chromosomes tested, N = 92 were Asian

TABLE 8

| Subject ID | Sex | Mutations | Clinical Details | Family History | Comments |
|---|---|---|---|---|---|
| Family 1 | M | 167-kb del | Meet ADI and ADOS-1 criteria for diagnosis of autism. Difficulty with conversations, echoed words, repetitive interests, delay in social use of language. Attention Deficit and Hyperactivity Disorder (ADHD). No mental retardation (MR). Non-Verbal IQ = 42% ile | Maternal history of learning problem and articulation difficulties. Paternal history of ADHD like features. | Severe colic during early childhood |
| Family 1 | M | 167-kb del | Meet ADI and ADOS-1 criteria for diagnosis of autism. Difficulty with conversations, echoed words, repetitive interests, delay in social use of language. Attention Deficit and Hyperactivity Disorder (ADHD). No mental retardation (MR). Non-Verbal IQ = 23% ile | Maternal history of learning problem and articulation difficulties. Paternal history of ADHD like features. | Severe colic during early childhood |
| Family 2 | M | I173V | Meet ADI and ADOS-1 criteria for diagnosis of autism. Highly repetitive language and behaviour, motor mannerisms, extremely hyperactive, poor motor coordination and mental retardation, Lang: receptive = 40, <1% ile, expressive = 40, <1% ile | Father had type II diabetes | |
| Family 3 | M | I173V | Meet ADI and ADOS-1 criteria for diagnosis of autism. Meet ADI and ADOS-1 criteria for diagnosis of autism. ADI social score = 25, ADI communication score = 21, ADI Restricted, Repetitive, and Stereotyped Behavior Score = 11, ADI development score = 3, Normal IQ, | No family history of PDD | |
| | M | V195I | Diagnosed with autism at the age of 3 years and 4 months. Meet ADI and ADOS-1 criteria for diagnosis of autism. Severe expressive and receptive language delay. No dysmorphology observed. | No family history of PDD | FRX and head CT scan was normal |
| Family 5 | M | ML336-7II | Meet ADI and ADOS-1 criteria for diagnosis of autism. ADI social score = 26, ADI communication score = 14, ADI stereotype score = 5 ADI development score: 4, ADOS social + communication score = 20, ADOS Restricted, Repetitive, and Stereotyped Behavior Score = 3, Some traits were observed that could be related to schizophrenia. | Father died of leukemia | Minor thalassemia |
| Family 6 | M | E479G | Diagnosed with high functioning autism. | No family history of PDD | |
| Family 7 | M | L73F | Meet ADI and ADOS-1 criteria for diagnosis of autism | | |

All these mutations resulted in the substitution of highly conserved amino acids, and were inherited from unaffected carrier mothers. Based on in silico protein modeling, three mutations (L73F, I173V, V195I) are present in a predicted amino acid loop that sits outside of the cell membrane. This loop is posited to interact with the ligand, Hh. Another mutation, the 2-amino acid substitution ML336-3371I was present within a predicted transmembrane domain. Finally, the E479G mutation was present within a predicted cytoplasmic amino acid loop. In five out of six families, these mutations segregated with the phenotype. Controls (439) were tested for the I173V and V195I mutations, 500 controls for ML336-3371I, and 282 controls for L73F and E479G. None of these mutations were present in controls. Furthermore, the fact that these mutations were all maternally inherited to male probands, and were not observed in our control populations, indicates that the mutations are associated with ASD. In turn, it is reasonable to assume that these mutations contribute to the etiology of autism, and perhaps in-combination with other disease-related loci, give rise to the ASD phenotype.

Interestingly, in two of the ASD families reported in Tables 7/8 (Family-2 & Family-4), other ASD-related CNVs were identified. In family 2, in addition to I173V mutation, a de novo ~1.0 Mb loss at 1p21.3 resulting in deletion of the entire DPYD gene (NM_000110.3) was identified. DPYD encodes a rate-limiting enzyme, dihydropyrimidine dehydrogenase (DPD), involved in pyrimidine metabolism. Complete DPD deficiency results in highly variable clinical outcomes, with convulsive disorders, motor retardation, and mental retardation being the most frequent manifestations. In Family-4, in addition to the V195I mutation, a 66 Kb de novo loss at 7q36.2 was identified resulting in deletion of DPP6 exon 3, and 33 amino acids towards the N-terminal end of the DPP6 protein. These cases evidence digenic involvement in ASD.

The ability of these. PTCHD1-mutants to repress Gli2 expression was compared with wild type to determine if there was loss of function in the mutants. NIH10T1/2 fibroblasts were transfected with CMV-empty vector, a Gli-responsive promoter fused to the Luciferase gene (Gli2 pro), β-Gal (normalization) and PTCHD1 mutant expression plasmids. A mild loss of function of at least the E479G and ML336-711 mutants resulted in increased expression of Gli2 compared to wild type.

The invention claimed is:

1. A method of detecting a sequence variation of a PTCHD1 gene in an individual, the method comprising:
   (a) amplifying a PTCHD1 nucleic acid in a biological sample comprising a PTCHD1 nucleic acid obtained from a human; (b) sequencing the PTCHD1 nucleic acid from the biological sample; and (c) detecting the presence of a sequence variant of PTCHD1, wherein the sequence variant of PTCHD1 is a sequence variant of PTCHD1 comprising an A to G mutation at a position corresponding to position 525 of SEQ ID NO: 17.

2. A method as defined in claim 1, additionally comprising detecting a sequence variant of PTCHD1 comprising a deletion of at least a portion of exon 1 of PTCHD1, wherein exon 1 of PTCHD1 corresponds to positions 1-359 of SEQ ID NO: 17.

3. The method of claim 1, wherein the nucleic acid obtained from a human is genomic DNA.

4. The method of claim 1, wherein the amplification comprises amplification with a primer pair of SEQ ID NO: 3 and SEQ ID NO: 4.

5. The method of claim 1, wherein additionally comprising detecting a sequence variant of PTCHD1 comprising a C to T mutation at a position corresponding to position 225 of SEQ ID NO: 17.

6. The method of claim 1, additionally comprising detecting a sequence variant of PTCHD1 comprising a G to A mutation at position corresponding to position 591 of SEQ ID NO: 17.

7. The method of claim 1, additionally comprising detecting a sequence variant of PTCHD1 comprising a GC to TA mutation at positions corresponding to positions 1016-1017 of SEQ ID NO: 17.

8. The method of claim 1, additionally comprising detecting a sequence variant of PTCHD1 comprising an A to G mutation at position 1444 of SEQ ID NO: 17.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
attcgcagtt ccttcgtctt                                              20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
aaagtggatt gatcggttcc                                              20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
gcttgaggac gtgtttctcc                                              20

<210> SEQ ID NO 4
<211> LENGTH: 19
<212> TYPE: DNA
<213> ORGANISM: Artificial
<220> FEATURE:
<223> OTHER INFORMATION: primer

<400> SEQUENCE: 4
ctaggagagg tggcgctct                                               19
```

<210> SEQ ID NO 5
<211> LENGTH: 17
<212> TYPE: DNA
<213> ORGANISM: Artificial
<220> FEATURE:
<223> OTHER INFORMATION: primer

<400> SEQUENCE: 5
agcgtgcgcc tcgccct                                                17

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
tccttgtcca ggaggctggg a                                           21

<210> SEQ ID NO 7
<211> LENGTH: 17
<212> TYPE: DNA
<213> ORGANISM: Artificial
<220> FEATURE:
<223> OTHER INFORMATION: primer

<400> SEQUENCE: 7
gcgcccgctc tgctcta                                                17

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
tccttgtcca ggaggctggg a                                           21

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
gaatgtccac cctctccaaa                                             20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
aaggctactc ctggcctttt                                             20

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
ctttgaccca gtagtccctc a                                            21

<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
gcacaaaccc cttggtgta                                               19

<210> SEQ ID NO 13
<211> LENGTH: 27
<212> TYPE: DNA
<213> ORGANISM: Artificial
<220> FEATURE:
<223> OTHER INFORMATION: primer

<400> SEQUENCE: 13
tgtgattggg ttttacatat atgagtc                                      27

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
aggtcagatt tgaaggcaca g                                            21

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
aaaaatgccc tggaagtgc                                               19

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
tgtgtgaatt ctcataacaa ctcct                                        25

<210> SEQ ID NO 17
<211> LENGTH: 5305
<212> TYPE: DNA
<213> ORGANISM: Homo sapiens

<400> SEQUENCE: 17
gctctaggat gctgcggcag gttctgcaca ggggcttgag gacgtgtttc tcccggctcg    60
gccacttcat tgccagtcac cctgtcttct tcgcctcggc gccggtgctc atctccatcc   120
tgctcggcgc cagcttcagc cgctaccagg tcgaggagag cgtggagcac ctgctggcgc   180

```
cccagcacag cctggccaag atcgagcgca acctcgttaa cagcctcttc ccggtcaacc      240
gctccaagca ccgtctctac tcggacctgc agaccccggg cgctacggc cgggtcatcg      300 tcacctcctt ccagaaagcc aacatgctgg accagcatca caccgacctg atcttaaagt    360
tgcatgctgc tgtcaccaag atccaggttc aaggcctgg tttaattac acgtttgccc      420 atatatgtat cctgaataat gataagactt gcatcgtgga tgacatagtg cacgtcctgg   480
aagagctaaa gaatgctcgg gccaccaatc ggaccaattt tgctatcaca tacccaatca    540
ctcacttaaa ggacgggagg gctgtgtaca atgggcacca gcttggggc gtcactgtgc    600 acagcaaaga ccgggtgaaa tctgcagagg ccatccagct cacctactac ctgcagtcaa   660
tcaacagtct caatgacatg gtgctgaga ggtgggagtc cagcttctgc gacactgtca    720
gactgtttca gaaatccaac agcaaagtca aatgtaccc ttacacgtcc tcctcactga    780
gggaagattt ccagaagacc agccgcgtat cagaacgtta cctggtcacc agcctgattc   840
tggtggttac catggccatc ctgtgttgct ctatgcagga ctgcgtccgc agcaaaccct  900
ggctaggcct gctcggattg gtgaccataa gcctggccac tctcactgca gccgggatca   960
tcaatcttac tggtgggaaa tataattcca ccttcctggg agtccctttc gtcatgctag  1020
gtcatggatt atatgggact tttgaaatgt tatcctcctg gaggaaaact agagaagacc  1080
aacatgttaa agagaaact gcagcagtct atgcagactc catgctctcc ttttctctca   1140
ccactgccat gtacctggtc accttttggca taggggccag ccctttcacg aacattgagg  1200
cagccaggat tttctgctgc aattcctgta ttgcaatctt cttcaactac ctctatgtac   1260
tctcgtttta tggttccagc ctagtgttca ctggctacat agaaaacaat taccagcata  1320
gtatcttctg tagaaaagtc ccaaagcctg aggcattgca ggagaagccg gcatggtaca  1380
ggtttctcct gacggccaga ttcagtgagg acacagctga aggcgaggaa gcgaacactt  1440
acgagagtca cctattggta tgtttcctca aacgctatta ctgtgactgg ataaccaaca  1500
cctatgtcaa gccttttgta gttctctttt accttattta tatttccttt gccttaatgg  1560
gctatctgca ggtcagtgaa gggtcagacc ttagtaacat tgtagcaacc gcgacacaaa  1620
ccattgagta cactactgcc cagcaaaagt acttcagcaa ctacagtcct gtgattgggt  1680
tttacatata tgagtctata gaatactgga acactagtgt ccaagaagat gttctagaat  1740
acaccaaggg gtttgtgcgg atatcctggt ttgagagcta tttaaattac cttcggaaac  1800
tcaatgtatc cactggcttg cctaagaaaa atttcacaga catgttgagg aattcctttc   1860
tgaaagcccc tcaattttca cattttcaag aggacatcat cttctctaaa aaatacaatg   1920
atgaggtcga tgtagtggcc tccagaatgt tttggtggc caagaccatg gaaacaaaca   1980
gagaagaact ctatgatctc ttggaaaccc tgaggagact ttctgtcacc tccaaggtga   2040
agttcatcgt cttcaatccg tccttttgtat acatggatcg atatgcctcc tctctgggag  2100
cccccctgca caactcctgc atcagtgctt tgttcctgct cttcttctcg gcattcctgg   2160
tggcagattc actgattaac gtctggatca ctctcacagt tgtgtccgtg gagtttggag   2220
tgataggttt catgacatta tggaaagtag aactggactg catttctgtg ctatgcttaa   2280
tttatggaat taattacaca attgacaatt gtgctccaat gttatccaca tttgttctgg   2340
gcaaggattt cacaagaact aaatgggtaa aaatgccct ggaagtgcat ggggtagcta    2400
ttttacagag ttacctctgc tatattgttg gtctgattcc tcttgcagct gtgccttcaa   2460
atctgacctg tacactgttc aggtgcttgt ttttaatagc atttgtcacc ttcttttcact   2520 gctttgccat tttacctgtg atactgactt tcctgccacc ctctaagaaa aaaggaaag    2580
```

```
agaagaaaaa tcctgagaac cgggaggaaa ttgagtgtgt agaaatggta gatatcgata    2640
gtacccgtgt ggttgaccaa attacaacag tgtgataatg tctgcttggc atattttcac    2700
cttaggtctt atcaagacca aagagattat gttaatgaaa caattaaatt caaagttctt    2760
ccctttttta aagataggaa acaggcattg ccaaaaaaaa aaaaaaaaaa aaaggaaag     2820 gacagtgggg agaaatgggc ctggcatatt ttcagtcttt aaaacaaagg agttgttatg    2880
agaattcaca cacacataga cacacacaca cacacacaca cacacacaca cacacacaca    2940
ccctgggaga cctatagtct cttaaactaa gatcaagtag aagaaagctt attaacaagc    3000
aggatcctgc cttatccaaa ctgcagatgt tgctggcatt gtgacaaaac ccactgattg    3060
aaaggtcaac tgccaaggca gaaacacctt taagcattgt tcaaacaata aggcttccag    3120
aacttctgta gagcagtagc tccagtcatg gtctgtggtt tgaggtttta gctgtctcac    3180
ctagctccct aacactgaag gagatacttg tgaaagttct gaccagcaaa agcaagccag    3240
agccttggaa actgatatgt ggtagagtgg ccatcactca tggactaaaa ttgattcacc    3300
gctaaattta cccaggtgaa gcagtttcgt tgtctagaat gaaattatca tattccgcca    3360
ttggtatgcc tttaacattt gtatagtttg gtttgcttaa acaccttaa aaccaatgac     3420 agctccagca ctgcagaatt ggtgtgattc tactttggaa tagcttgtca cttgtcacca    3480
aatgggtctg cttttattagt tacagctctt ggcaggagga tccagggacc caaaaccaca   3540
gggccaaacc caaatacctg gcatgatgga gcaaaagcag gtgtctactt ggacccagat    3600
atagtgtctc cattttaaca acaacaacaa aatagccagc tggtacagct gtttgcattg    3660
gccctacatg cattttttgc atggatatcc agaaacatct gcccacacaa aactgcgggg    3720
aaaaaaaatg aacactgaaa tagttatttg ctgttgcttc caacttgtag tgccagtctg    3780
cctttgctgt gaaacacacc tgctcagaga cagagagggg aagaagatct ttggtaagtc    3840
taagtcctga cgctgagaag ctttgtaaaa gtgcagggag ataaagggcc aaaagggaga    3900
tagatggaaa acactggaaa aagtattcac tgatacaaat ctatcaatga tggcagtcca    3960
attctcttgc taaagtggct gcacctcacc ttgctggtcc cccccacacc ttttttgatg    4020
tccttctgcg tcatcatagc aaggcccttc tgtaaattaa caagcctaga tatttatact    4080
cttgacttcc agtatctaca gaagaatggt tcatagatct aaacagaaat ggtttagatc    4140
taaaaaggct gtatacgttg cccaggcccc tgcattcttt taaatttata aaatgaagc     4200 taaaacctgg ttacatttga agcaaatatc tacagtattt ttccctttta gagatgtagc    4260
ttccttagac atctgtagtg gtaagcattt cccaaaagca tcttaccttt ctgaaccttta   4320 gcagacatac tgtgcagctt acctatcttc tgcagaggag gaaactgaga cctaggagaa    4380
taaagtgact cactcaggtc acaccactaa agggttttca tcatttcagc atacctaaga    4440
cagggcagtc caattttcag tattctcata agatggctat tactcctctc aaaatgcatt    4500
tccaaagtag gaacatagga cttcgttggc cacagggcag acattttttt agtgtctgga    4560
attaaaatgt ttgaggttta ggtttgccat tgtctttcca aaaggccaaa taattcagat    4620
gtaaccacac caagtgcaaa cctgtgcttt ctatttcacg tactgttgtc catacagttc    4680
taaatacatg tgcagggat tgtagctaat gcattacaca gtcgttcagt cttctctgca     4740
gacacactaa gtgatcatac caacgtgtta tacactcaac tagaagataa taagctttaa   4800
tctgagggca agtacagtcc tgacaaaagg gcaagtttgc ataatagatc ttcgatcaat    4860
tctctctcca aggggcccgc aactaggcta ttattcataa aacacaactg aagagggat     4920
```

```
tggttttact gttaaatcat gtgttgctaa atcattttct gaacagtgtg ttctaaatca    4980
gtcattgatt tagtgtcagc cacgtggagc acctcggctt aaagcagctc cacaaaacct    5040
gacacaacac acacaccaat taaatggatt ttgttgagaa tttaatcatt caatttggtc    5100
aaccagaatg acttcctgtg gaactctgtt ttatgacaga taatagtttt ccaacttgat    5160
tgagtctctg tatacccctgg gatattgtat tttttaatga agggcatttt caaacttgtc    5220
aacttctctt ttcagcactt gaaatgaagg cttatggaat tctgactgtg aaatgaattt    5280
ttctattggg aaaaaaaaaa aaaaa                                          5305
```

<210> SEQ ID NO 18
<211> LENGTH: 888
<212> TYPE: PRT
<213> ORGANISM: Homo sapiens

<400> SEQUENCE: 18

```
Met Leu Arg Gln Val Leu His Arg Gly Leu Arg Thr Cys Phe Ser Arg
1               5                   10                  15

Leu Gly His Phe Ile Ala Ser His Pro Val Phe Ala Ser Ala Pro
            20                  25                  30

Val Leu Ile Ser Ile Leu Leu Gly Ala Ser Phe Ser Arg Tyr Gln Val
        35                  40                  45

Glu Glu Ser Val Glu His Leu Leu Ala Pro Gln His Ser Leu Ala Lys
    50                  55                  60

Ile Glu Arg Asn Leu Val Asn Ser Leu Phe Pro Val Asn Arg Ser Lys
65                  70                  75                  80

His Arg Leu Tyr Ser Asp Leu Gln Thr Pro Gly Arg Tyr Gly Arg Val
                85                  90                  95

Ile Val Thr Ser Phe Gln Lys Ala Asn Met Leu Asp Gln His His Thr
            100                 105                 110

Asp Leu Ile Leu Lys Leu His Ala Ala Val Thr Lys Ile Gln Val Pro
        115                 120                 125

Arg Pro Gly Phe Asn Tyr Thr Phe Ala His Ile Cys Ile Leu Asn Asn
    130                 135                 140

Asp Lys Thr Cys Ile Val Asp Asp Ile Val His Val Leu Glu Glu Leu
145                 150                 155                 160

Lys Asn Ala Arg Ala Thr Asn Arg Thr Asn Phe Ala Ile Thr Tyr Pro
                165                 170                 175

Ile Thr His Leu Lys Asp Gly Arg Ala Val Tyr Asn Gly His Gln Leu
            180                 185                 190

Gly Gly Val Thr Val His Ser Lys Asp Arg Val Lys Ser Ala Glu Ala
        195                 200                 205

Ile Gln Leu Thr Tyr Tyr Leu Gln Ser Ile Asn Ser Leu Asn Asp Met
    210                 215                 220

Val Ala Glu Arg Trp Glu Ser Ser Phe Cys Asp Thr Val Arg Leu Phe
225                 230                 235                 240

Gln Lys Ser Asn Ser Lys Val Lys Met Tyr Pro Tyr Thr Ser Ser Ser
                245                 250                 255

Leu Arg Glu Asp Phe Gln Lys Thr Ser Arg Val Ser Glu Arg Tyr Leu
            260                 265                 270

Val Thr Ser Leu Ile Leu Val Val Thr Met Ala Ile Leu Cys Cys Ser
        275                 280                 285

Met Gln Asp Cys Val Arg Ser Lys Pro Trp Leu Gly Leu Leu Gly Leu
    290                 295                 300
```

```
Val Thr Ile Ser Leu Ala Thr Leu Thr Ala Ala Gly Ile Ile Asn Leu
305                 310                 315                 320

Thr Gly Lys Tyr Asn Ser Thr Phe Leu Gly Val Pro Phe Val Met
            325                 330                 335

Leu Gly His Gly Leu Tyr Gly Thr Phe Glu Met Leu Ser Ser Trp Arg
                340                 345                 350

Lys Thr Arg Glu Asp Gln His Val Lys Glu Arg Thr Ala Ala Val Tyr
            355                 360                 365

Ala Asp Ser Met Leu Ser Phe Ser Leu Thr Thr Ala Met Tyr Leu Val
            370                 375                 380

Thr Phe Gly Ile Gly Ala Ser Pro Phe Thr Asn Ile Glu Ala Ala Arg
385                 390                 395                 400

Ile Phe Cys Cys Asn Ser Cys Ile Ala Ile Phe Phe Asn Tyr Leu Tyr
                405                 410                 415

Val Leu Ser Phe Tyr Gly Ser Ser Leu Val Phe Thr Gly Tyr Ile Glu
            420                 425                 430

Asn Asn Tyr Gln His Ser Ile Phe Cys Arg Lys Val Pro Lys Pro Glu
            435                 440                 445

Ala Leu Gln Glu Lys Pro Ala Trp Tyr Arg Phe Leu Leu Thr Ala Arg
450                 455                 460

Phe Ser Glu Asp Thr Ala Glu Gly Glu Glu Ala Asn Thr Tyr Glu Ser
465                 470                 475                 480

His Leu Leu Val Cys Phe Leu Lys Arg Tyr Tyr Cys Asp Trp Ile Thr
                485                 490                 495

Asn Thr Tyr Val Lys Pro Phe Val Val Leu Phe Tyr Leu Ile Tyr Ile
            500                 505                 510

Ser Phe Ala Leu Met Gly Tyr Leu Gln Val Ser Glu Gly Ser Asp Leu
            515                 520                 525

Ser Asn Ile Val Ala Thr Ala Thr Gln Thr Ile Glu Tyr Thr Thr Ala
530                 535                 540

Gln Gln Lys Tyr Phe Ser Asn Tyr Ser Pro Val Ile Gly Phe Tyr Ile
545                 550                 555                 560

Tyr Glu Ser Ile Glu Tyr Trp Asn Thr Ser Val Gln Glu Asp Val Leu
                565                 570                 575

Glu Tyr Thr Lys Gly Phe Val Arg Ile Ser Trp Phe Glu Ser Tyr Leu
            580                 585                 590

Asn Tyr Leu Arg Lys Leu Asn Val Ser Thr Gly Leu Pro Lys Lys Asn
            595                 600                 605

Phe Thr Asp Met Leu Arg Asn Ser Phe Leu Lys Ala Pro Gln Phe Ser
610                 615                 620

His Phe Gln Glu Asp Ile Ile Phe Ser Lys Lys Tyr Asn Asp Glu Val
625                 630                 635                 640

Asp Val Val Ala Ser Arg Met Phe Leu Val Ala Lys Thr Met Glu Thr
                645                 650                 655

Asn Arg Glu Glu Leu Tyr Asp Leu Leu Glu Thr Leu Arg Leu Ser
            660                 665                 670

Val Thr Ser Lys Val Lys Phe Ile Val Phe Asn Pro Ser Phe Val Tyr
            675                 680                 685

Met Asp Arg Tyr Ala Ser Ser Leu Gly Ala Pro Leu His Asn Ser Cys
            690                 695                 700

Ile Ser Ala Leu Phe Leu Leu Phe Phe Ser Ala Phe Leu Val Ala Asp
705                 710                 715                 720

Ser Leu Ile Asn Val Trp Ile Thr Leu Thr Val Val Ser Val Glu Phe
```

-continued

```
                725                 730                 735
Gly Val Ile Gly Phe Met Thr Leu Trp Lys Val Glu Leu Asp Cys Ile
            740                 745                 750

Ser Val Leu Cys Leu Ile Tyr Gly Ile Asn Tyr Thr Ile Asp Asn Cys
            755                 760                 765

Ala Pro Met Leu Ser Thr Phe Val Leu Gly Lys Asp Phe Thr Arg Thr
    770                 775                 780

Lys Trp Val Lys Asn Ala Leu Glu Val His Gly Val Ala Ile Leu Gln
785                 790                 795                 800

Ser Tyr Leu Cys Tyr Ile Val Gly Leu Ile Pro Leu Ala Ala Val Pro
            805                 810                 815

Ser Asn Leu Thr Cys Thr Leu Phe Arg Cys Leu Phe Leu Ile Ala Phe
            820                 825                 830

Val Thr Phe Phe His Cys Phe Ala Ile Leu Pro Val Ile Leu Thr Phe
            835                 840                 845

Leu Pro Pro Ser Lys Lys Lys Arg Lys Glu Lys Lys Asn Pro Glu Asn
    850                 855                 860

Arg Glu Glu Ile Glu Cys Val Glu Met Val Asp Ile Asp Ser Thr Arg
865                 870                 875                 880

Val Val Asp Gln Ile Thr Thr Val
            885
```